US008845879B2

(12) United States Patent
Minteer et al.

(10) Patent No.: US 8,845,879 B2
(45) Date of Patent: Sep. 30, 2014

(54) ORGANELLE BIOELECTRODES AND METHODS OF MAKING AND USING THE SAME

(75) Inventors: Shelley Minteer, St. Louis, MO (US); Abdul Waheed, Valley Park, MO (US)

(73) Assignee: Saint Louis Univesrity, Saint Louis, MO (US)

( * ) Notice: Subject to any disclaimer, the term of this patent is extended or adjusted under 35 U.S.C. 154(b) by 242 days.

(21) Appl. No.: 13/301,773

(22) Filed: Nov. 21, 2011

(65) Prior Publication Data

US 2012/0138485 A1  Jun. 7, 2012

Related U.S. Application Data

(60) Provisional application No. 61/514,432, filed on Aug. 2, 2011, provisional application No. 61/417,123, filed on Nov. 24, 2010.

(51) Int. Cl.
*G01N 27/327* (2006.01)
*B05D 5/12* (2006.01)
*G01N 33/50* (2006.01)

(52) U.S. Cl.
CPC .................... *G01N 33/5076* (2013.01)
USPC .... 205/777.5; 205/775; 422/68.1; 422/82.01; 435/287.1; 435/177; 429/401

(58) Field of Classification Search
USPC ............... 429/401; 205/777.5, 775; 422/68.1, 422/82.01; 435/287.1, 177; 204/403.01
See application file for complete search history.

(56) References Cited

U.S. PATENT DOCUMENTS

| 7,141,369 B2 | 11/2006 | Cao |
| 2003/0124572 A1 | 7/2003 | Umek et al. |
| 2008/0261085 A1* | 10/2008 | Sastry et al. ...................... 429/2 |
| 2009/0305089 A1 | 12/2009 | Minteer et al. |

FOREIGN PATENT DOCUMENTS

| WO | 2008082694 | | 7/2008 |
| WO | WO 2008/082694 | * | 7/2008 |
| WO | WO/2008/082694 | * | 7/2008 |
| WO | WO/2008/137846 | * | 11/2008 |

OTHER PUBLICATIONS

Schubert et al., Methods in Enzymology, vol. 137, 1988.*
Sarma et al., Biosensors and Bioelectronics, 24, available online Oct. 18, 2008, 2313-2322.*

(Continued)

*Primary Examiner* — Jennifer Dieterle
(74) *Attorney, Agent, or Firm* — Husch Blackwell LLP; Mark E. Stallion, Esq.

(57) ABSTRACT

A method for monitoring the metabolic state of an organelle in the presence of a potential organelle modulating agent is disclosed. A first organelle-modified bioelectrode is provided that is electrically coupled to a second electrode of opposite polarity in a circuit. The first bioelectrode is contacted with an aqueous carrier containing a biologically acceptable electrolyte and an effective amount of a potential organelle modulating agent and an effective amount of an organelle substrate. The substrate is reacted at the bioelectrode to form an ionic product that is released into the aqueous carrier-containing electrolyte to thereby provide a current at the second electrode when the circuit is closed. A metabolic flux data set is obtained during the reaction and is compared to a control metabolic flux data set obtained under the same conditions in the absence of the organelle modulating agent, thereby determining the metabolic state of the organelle.

16 Claims, 15 Drawing Sheets

(56) References Cited

OTHER PUBLICATIONS

Arechederra et al., Analyst, 2011, 135, 3747-3752.*

Germain, et al., Nitroaromatic Actuation of Mitochondrial Bioelectrocatalysis for Self-Powered Explosive Sensors; Journal of the American Chemical Society 130, 15272-15273 (2008).

Thomas, et al., Effects of annealing on mixture-cast membranes of Nafion and quaternary ammonium bromide salts, Journal of Membrane Science 213 (2003) 55-66.

Moore, et al. Improving the Environment for Immobilized Dehydrogenase Enzymes by Modifying Nafion with Tetraalkylammonium Bromides, Biomacromolecules 5 (2004) 1241-1247.

Klotzbach, et al., Effects of hydrophobic modification of chitosan and Nafion on transport properties, ion-exchange capacities, and enzyme immobilization; Journal of Membrane Science 282 (2006) 276-283.

Moore, et al., Effects of surfactants on the transport properties of redox species through Nafion membranes; Journal of Membrane Science 255 (2005) 233-238.

Addo, et al., Evaluating Enzyme Cascades for Methanol/Air Biofuel Cells Based on NADþ-Dependent Enzymes; Electroanalysis, vol. 22, No. 7-8, pp. 807-812 (2010).

Arechederra, et al., Organelle-based biofuel cells: Immobilized mitochondria on carbon paper electrodes, Electrochimica Acta 53, 6698-6703 (2008).

Arechederra, et al., Mitochondrial bioelectrocatalysis for biofuel cell applications; Electrochimica Acta 54, 7268-7273 (2009).

Mabalirajan et al., Mitochondrial Structural Changes and Dysfunction Are Associated with Experimental Allergic Asthma; The Journal of Immunology; vol. 181, 3540-3548 (2008).

Scatena, et al., The role of mitochondria in pharmacotoxicology: a reevaluation of an old, newly emerging topic; Am. J. Physiol. 293, C12-C21, (2007).

Boelsterli et al., The heterozygous Sod2+/− mouse: modeling the mitochondrial role in drug toxicity, Drug Discovery Today 13, 982-988, (2008).

Degli Esposti et al., Natural substances (acetogenins) from the family Annonaceae are powerful inhibitors of mitochondrial NADH dehydrogenase (Complex I)Biochem. J. 301, 161-167 (1994).

Dykens et al., The significance of mitochondrial toxicity testing in drug development; Drug Discovery Today 12, 777-785, (2007).

Dykens et al., Strategies to reduce late-stage drug attrition due to mitochondrial toxicity; Expert Review of Molecular Diagnostics 7, 161-175 (2007).

Kovacic et al., Mechanism of Mitochondrial Uncouplers, Inhibitors, and Toxins: Focus on Electron Transfer, Free Radicals, and Structure-Activity Relationships; Current Medicinal Chemistry 12, 2601-2623 (2005).

Mabalirajan et al., Esculetin Restores Mitochondrial Dysfunction and Reduces Allergic Asthma Features in Experimental Murine Model; Journal of Immunology. 183, 2059-2067 (2009).

Nadanaciva et al., Current Concepts in Drug-Induced Mitochondrial Toxicity; Current Protocols in Toxicology 2, 1-9, (May 2009).

Petit et al., Mitochondria are sensors for HIV drugs; Trends in Pharmacological Sciences 26, 258-264 (2005).

Wang et al., Inhibitors of Cytochrome c Release with Therapeutic Potential for Huntington's Disease Journal of Neuroscience 28, 9473-9485 (Sep. 2008).

Yang, et al., Apoptosis of murine lupus T cells induced by the selective cyclooxygenase-2 inhibitor celecoxib: Molecular mechanisms and therapeutic potential; International Immunopharmacology 7, 1411-1421 (2007).

Hatefi et al., Inhibitors and Activators of the Mitochondrial Reduced Diphosphopyridine Nucleotide Dehydrogenase; Journal of Biological Chemistry; 244, 2358-2365 (1969).

Wojtczak et al., Basic Mitochondrial Physiology in Cell Viability and Death, John Wiley & Sons, New York, 1-36 (2008).

Dröse et al., Ambivalent effects of diazoxide on mitochondrial ROS production at respiratory chain complexes I and III; Biochimica et Biophysica Acta 1790 (2009) 558-565.

Nagao et al., Human mitochondrial carbonic anhydrase: cDNA cloning, expression, subcellular localization, and mapping to chromosome 16 Proc. Natl. Acad. Sci. USA vol. 90, 7623-7627 (Aug. 1993).

Nagao et al., Mitochondrial carbonic anhydrase (isozyme V) in mouse and rat:cDNA cloning, expression, subcellular localization, processing, and tissue distribution; Proc. Natl. Acad. Sci. USA vol. 91, 10330-10334 (Oct. 1994).

Maurer, et al., Lithium-induced enhancement of mitochondrial oxidative phosphorylation in human brain tissue; Bipolar Disorders, vol. 11, pp. 515-522, 2009.

* cited by examiner

ORGANELLE BIOELECTRODES AND METHODS OF MAKING AND USING THE SAME

CROSS REFERENCE

This application claims the benefit of and priority to U.S. Provisional Patent Application Ser. No. 61/417,123 filed Nov. 24, 2010 entitled Organelle Bioelectrodes And Methods Of Making And Using The Same, and further claims the benefit of U.S. Provisional Patent Application Ser. No. 61/514,432 filed Aug. 2, 2011 entitled Mitochondrial Bioelectrodes and Methods Of Making and Using The Same, the entirety of both of which are incorporated by reference herein in their entirety.

GOVERNMENTAL SUPPORT

The present invention was made with governmental support pursuant to grants 3-02186 from the National Science Foundation and 3-00473 from the United States Air Force Office of Scientific Research. The government has certain rights in the invention.

BACKGROUND OF THE INVENTION

Screening of mitochondrial function in the presence of drug compounds is becoming of increased interest because, as more research accumulates for fundamental drug mechanisms and fundamental causes of disease, more is being discovered that points directly to mitochondria function. [Boelsterli et al., *Drug Discovery Today* 13, 982-988, (2008); Degli Esposti et al., *Biochem. J.* 301, 161-167 (1994); Dykens et al., *Drug Discovery Today* 12, 777-785, (2007); Kovacic et al., *Current Medicinal Chemistry* 12, 2601-2623 (2005); Mabalirajan et al., *J. Immunol.* 181, 3540-3548 (2008); Mabalirajan et al., *J. Immunol.* 183, 2059-2067 (2009); Nadanaciva et al., *Current Protocols in Toxicology* 2, 1-9, (2009); Petit et al., *Trends in Pharmacological Sciences* 26, 258-264 (2005); Scatena et al., *Am. J. Physiol.* 293, C12-C21, (2007); Wang et al., *J. Neuroscience* 28, 9473-9485 (2008); Yang et al., *Int. Immunopharmacol.* 7, 1411-1421 (2007).]

One classic example is the treatment of bipolar disorder with lithium salts. Until recently, the fundamental mechanism of action has been unknown. The use of lithium salts can be traced back over 100 years ago for the treatment of mania. In 1970, the FDA approved its use as a treatment for bipolar disorder, and it has been heavily used ever since. Clinically, the mechanism was traced to the cell/tissue level, but the molecular biology was still uncertain.

In the last few years, research has shown that the lithium ion stimulates oxidative phosphorylation in the mitochondria by acting as an activator for the electron transport chain [Maurer et al., *Bipolar Disorders* 11, 515-522 (2009)]. In another example, several potent analgesics, including Demerol and barbiturates, reversibly inhibit Complex I of the electron transport chain causing the nerve cells to not be as active thereby reducing the pain an individual is experiencing [Hatefi et al., *J. Biol. Chem.* 244, 2358-2365 (1969)]. In cancer cells, the mitochondrial activity is suppressed because most of the metabolism is routed through glycolysis to produce lactate. This suppression also causes the programmed cell death, which is caused by the cytochrome release of the mitochondria to be directly suppressed thereby allowing the cancer cell to achieve its out of control state. If a therapeutic compound is targeted to specific complexes and proteins of the mitochondria then the therapeutic could effectively gain control of the mitochondria and stabilize the cell function or allow the cell to achieve programmed cell death, as in the case of cancer.

It is clear mitochondria are important to cell function due to their important role in energy conversion, but they are also important in calcium homeostasis, heme synthesis, steroid synthesis, and programmed cell death [Wojtczak et al., *Basic Mitochondrial Physiology in Cell Viability and Death*, John Wiley & Sons, New York, 1-36 (2008)]. Mitochondrial dysfunction is increasingly being found to be the cause of drug-induced toxicities. Pharmaceutical companies are therefore realizing the importance of early identification of drug effects of mitochondrial function in order to avoid late-stage attrition during drug development [Dykens et al., *Drug Discovery Today* 12, 777-785 (2007); Dykens et al., *Expert Review of Molecular Diagnostics* 7, 161-175 (2007)]. Many screening strategies are being developed to screen chemical drug libraries early in the drug development cycle for mitochondrial dysfunction.

Mitochondrial screening has not been part of the preclinical drug development process for four primary reasons: (1) it is difficult to accurately assess mitochondrial function; (2) there is no high throughput method for screening drug candidates; (3) drug companies did not fully understand how common mitochondrial dysfunction was a cause of drug toxicity; and the lack of evidence as to whether in vitro responses correspond to in vivo outcomes [Dykens et al., *Drug Discovery Today* 12, 777-785 (2007); Dykens et al., *Expert Review of Molecular Diagnostics* 7, 161-175 (2007)]. Although there are a variety of methods that are used to study mitochondrial function/dysfunction from animal models, these methods are time consuming and do not lend themselves to high throughput methods because it takes time for cell or organism growth, drug treatment, and waiting for cell death. Moreover, cell death is not necessarily the best method for studying mitochondrial dysfunction because it is an indirect method.

SUMMARY OF THE INVENTION

There is a need in the art for an assay for studying drug-induced and genetic mutation-induced mitochondrial dysfunction/function. As disclosed hereinafter, utilizing a proactive approach to discovery of a modulator such as a drug that affects organelle function and mechanisms of that function, and building on previous work of using whole viable immobilized organelles such as mitochondria to generate electricity on an electrode [Arechederra et al., *Electrochim. Acta* 53, 6698-6703 (2008); Germain et al., *J. Am. Chem. Soc.* 130, 15272-15273 (2008); Arechederra et al., *Electrochimica Acta* 54, 7268-7273 (2009); Addo et al., *Analyst* (In Preparation) (2010)], a method for monitoring organelle metabolism in response to a potential modulator using a mass-fabricated organelle electrode has been invented.

In the search of cures for cancer, diabetes, asthma, obesity, and many other diseases, many potential therapeutics have been found to negatively affect mitochondrial function, causing unwanted side effects. However, there are also numerous potential and current therapeutic agents that act by altering mitochondrial pathways and function in a beneficial manner causing a desired physiological effect.

A method for monitoring the metabolic state of an organelle in the presence of a potential organelle modulating agent is contemplated herein. That method comprises the steps of providing at least a first organelle-modified bioelectrode that is electrically coupled to a second electrode of opposite polarity in a circuit. The bioelectrode is contacted with an aqueous carrier that can contain a further fluid, gas, solid, or mixture thereof and contains an electrolyte, an effective amount of a potential organelle modulating agent and an effective amount of an organelle substrate. The substrate-containing carrier is reacted at the bioelectrode to form an ionic product from the substrate that is released into the aqueous carrier-containing electrolyte to thereby provide a current at the second electrode when the circuit is closed. A metabolic flux data set is obtained during the reaction using one or both of those electrodes and compared to a control metabolic flux data set obtained under the same conditions in the absence of the potential organelle modulating agent, thereby determining the metabolic state of the organelle in the presence of the potential organelle modulating agent.

In accordance with the above method, an illustrative approach has been developed for directly assaying mitochondrial metabolic activity as a function of metabolic substrate to determine drug toxicity. By wiring mouse or yeast mitochondria to a carbon electrode surface, electrons can be intercepted from Complex IV in the electron transport chain before they can reduce oxygen. The intercepted electrons are rerouted, so that oxygen reduction can occur at a separate electrode, the cathode. This permits the direct measurement of electrical current and potential of the mitochondria during their metabolism of substrates like pyruvate, fatty acids, amino acids, and Kreb's cycle intermediates as a measure of metabolic flux when there are different concentrations of drug compound present. Mitochondria from animals, yeast/fungi and plants can be used, such as those from a mouse, rat, potato, or yeast.

This technique provides for the development of high throughput mitochondrial drug candidate screening, as well as other applications where the quantitative study of mitochondrial activity is of interest. One example of a bioelectrode or biofuel cell suitable for use in the present invention is disclosed in International Publication Number WO 2008/082694 A2 entitled "Organelles in Bioanodes, Biocathodes, and Biofuel Cells", whose disclosures are hereby incorporated by reference. U.S. Provisional Patent Application Ser. No. 61/417,123 filed Nov. 24, 2010 entitled Organelle Bioelectrodes And Methods Of Making And Using The Same, to which this application claims priority is hereby incorporated by reference herein in its entirety.

BRIEF DESCRIPTION OF THE DRAWINGS

The accompanying drawings form a part of the specification and are to be read in conjunction therewith.

DETAILED DESCRIPTION OF THE INVENTION

Figure 1:
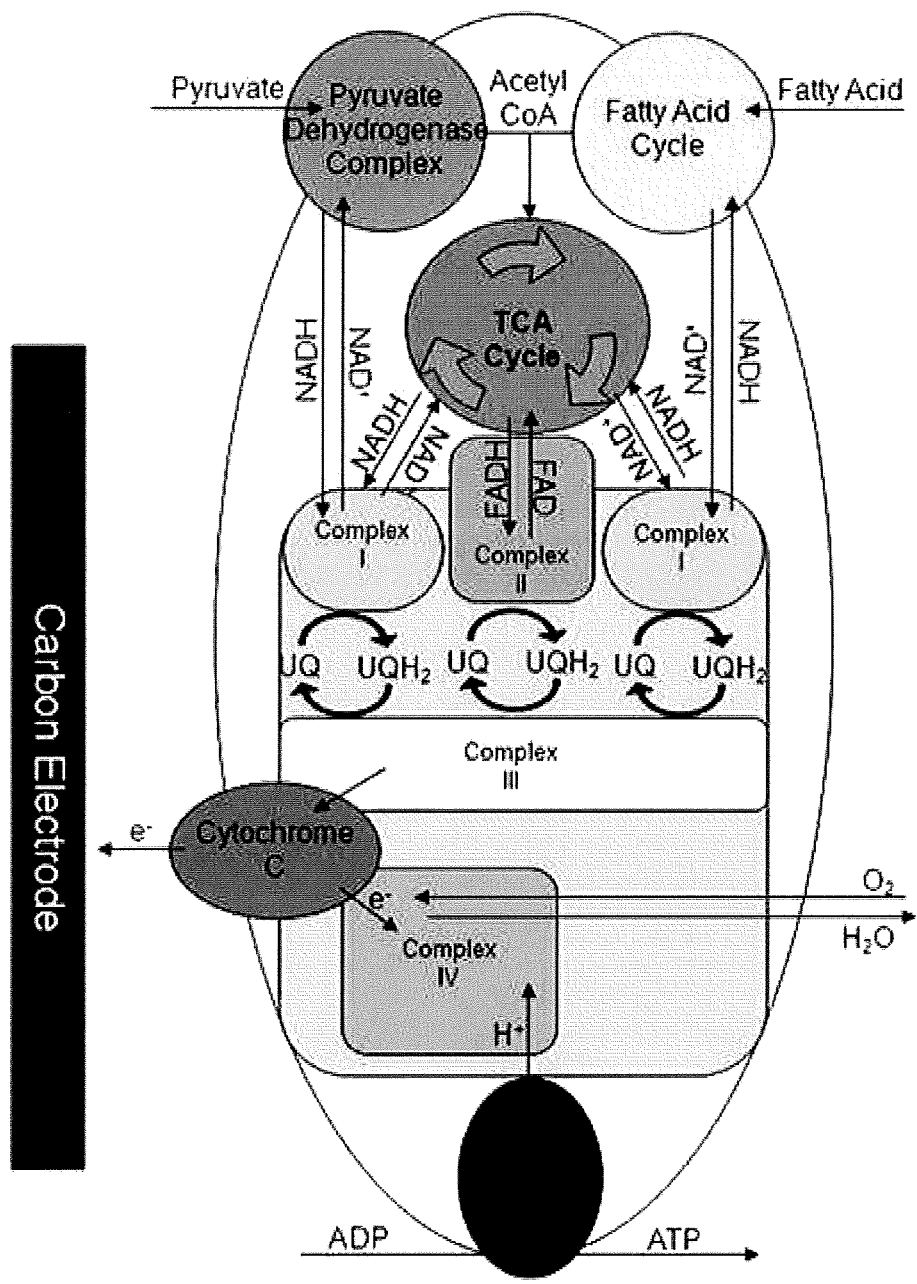
FIG. 1 is a schematic representation of the mechanism of electron transfer of mitochondria to an electrode surface in accordance with certain embodiments of the present invention.

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

A high throughput drug screening assay is contemplated. One embodiment contemplates an in vitro non-human and non-animal assay for screening potentially active compounds for causing mitochondrial dysfunction, which is currently done by animal testing further down the drug development pathway—this assay permits one to test drug or mitochondrial active compound candidates for mitochondrial toxicity at an earlier stage and more inexpensively. A second embodiment contemplates a quantitative determination of effects of a mitochondrial drug or active compound on metabolism.

In addition, a contemplated method permits synergistic compounds to be examined, where one compound alone may or may not have an effect, but when used in addition to another compound provides an enhanced effect or entirely different effect, or a return to normal function. In certain embodiments, the present invention can also be used in connection with water treatment and testing as well as treatment of and testing for biological agents including but not limited to pesticides, herbicides, antibiotics, hormones, poisons, warfare agents, and environmental contaminants that affect organelles such as mitochondria.

A method for monitoring the metabolic state of an organelle in the presence of a potential organelle modulating agent is contemplated. An organelle, in cell biology and herein, is a specialized subunit within a cell that has a specific function, that is usually separately enclosed within its own lipid bilayer or monolayer, and is typically within the cytoplasm of a cell. Major animal cell organelles and cellular structures include: (1) a nucleolus, (2) a nucleus, (3) a ribosome, (4) a vesicle, (5) a rough endoplasmic reticulum, (6) a Golgi apparatus, (7) cytoskeleton, (8) a smooth endoplasmic reticulum, (9) a mitochondrion, (10) a mitoplast, (11) a vacuole, (12) a lysosome, and (13) a centriole. Plant organelles include chloroplasts and thylakoids.

A contemplated method comprises the steps of providing at least a first organelle-modified bioelectrode that is electrically coupled to a second electrode of opposite polarity in a circuit. The organelle-modified bioelectrode is preferably free of a polymeric covering such as an ionomer layer over (on top of) the organelle. The bioelectrode is contacted with an aqueous carrier that contains an electrolyte, an effective amount of a potential organelle modulating agent, an effective amount of an organelle fuel as organelle substrate, and can optionally contain a further fluid, gas, solid, or mixture thereof and. The substrate-containing (fuel containing) carrier is reacted at the bioelectrode to form an ionic product from the substrate (fuel) that is released into the aqueous carrier-containing electrolyte to thereby provide a current at the second electrode when the circuit is closed. A metabolic flux data set is obtained during the reaction and compared to a control metabolic flux data set obtained under the same conditions in the absence of the organelle modulating agent, thereby determining the metabolic state of the organelle in the presence of the potential organelle modulating agent.

Referring to FIG. 1, a dominant role for the mitochondria is the production of ATP, as reflected by the large number of proteins in the inner membrane for this task. This is done by oxidizing the major products of glucose, pyruvate, and NADH, which are produced in the cytosol. This process of cellular respiration, also known as aerobic respiration, is dependent on the presence of oxygen. When oxygen is limited, the glycolytic products will be metabolized by anaerobic respiration, a process that is independent of the mitochondria. The production of ATP from glucose has an approximately 13-fold higher yield during aerobic respiration compared to anaerobic respiration.

Embedded in the inner membrane are proteins and complexes of molecules that are involved in the process called electron transport. The electron transport system (ETS), as it is called, accepts energy from carriers in the matrix and stores it to a form that can be used to phosphorylate ADP. Two energy carriers are known to donate energy to the ETS, namely nicotine adenine dinucleotide (NAD) and flavin adenine dinucleotide (FAD). Reduced NAD carries energy to complex I (NADH-Coenzyme Q Reductase) of the electron transport chain. FAD is a bound part of the succinate dehydrogenase complex (complex II).

It is reduced when the substrate succinate binds the complex. What happens when NADH binds to complex I? It binds to a prosthetic group called flavin mononucleotide (FMN), and is immediately re-oxidized to NAD. NAD is "recycled," acting as an energy shuttle. FMN receives the hydrogen from the NADH and two electrons. It also picks up a proton from the matrix. In this reduced form, it passes the electrons to iron-sulfur clusters that are part of the complex, and forces two protons into the inter-membrane space.

Electrons pass from complex I to a carrier (Coenzyme Q) embedded by itself in the membrane. From Coenzyme Q electrons are passed to a complex III which is associated with another proton translocation event. From Complex III the pathway is to cytochrome c then to a Complex IV (cytochrome oxidase complex). More protons are translocated by Complex IV, and it is at this site that oxygen binds, along with protons, and using the electron pair and remaining free energy, oxygen is reduced to water. Since molecular oxygen is diatomic, it actually takes two electron pairs and two cytochrome oxidase complexes to complete the reaction sequence for the reduction of oxygen. This last step in electron transport serves the critical function of removing electrons from the system so that electron transport can operate continuously.

The reduction of oxygen is not an end in itself. Oxygen serves as an electron acceptor, clearing the way for carriers in the sequence to be reoxidized so that electron transport can continue. Electron transport inhibitors act by binding one or more electron carriers, preventing electron transport directly. Changes in the rate of dissipation of the chemiosmotic gradient have no effect on the rate of electron transport with such inhibition. In fact, if electron transport is blocked the chemiosmotic gradient cannot be maintained. No matter what substrate is used to fuel electron transport, only two entry points into the electron transport system are known to be used by mitochondria. A consequence of having separate pathways for entry of electrons is that an ETS inhibitor can affect one part of a pathway without interfering with another part. Respiration can still occur depending on choice of substrate. An inhibitor may competely block electron transport by irreversibly binding to a binding site.

Each pyruvate molecule produced by glycolysis is actively transported across the inner mitochondrial membrane, and into the matrix where it is oxidized and combined with coenzyme A to form $CO_2$, acetyl-CoA, and NADH. The acetyl-CoA is the primary substrate to enter the citric acid cycle, also known as the tricarboxylic acid (TCA) cycle or Krebs cycle. The enzymes of the citric acid cycle are located in the mitochondrial matrix, with the exception of succinate dehydrogenase, which is bound to the inner mitochondrial membrane as part of Complex II. The citric acid cycle oxidizes the acetyl-CoA to carbon dioxide, and, in the process, produces reduced cofactors (three molecules of NADH and one molecule of $FADH_2$) that are a source of electrons for the electron transport chain, and a molecule of GTP (that is readily converted to an ATP).

The redox energy from NADH and $FADH_2$ is transferred to oxygen ($O_2$) in several steps via the electron transport chain. These energy-rich molecules are produced within the matrix via the citric acid cycle but are also produced in the cytoplasm by glycolysis. Reducing equivalents from the cytoplasm can be imported via the malate-aspartate shuttle system of antiporter proteins or feed into the electron transport chain using a glycerol phosphate shuttle.

Protein complexes in the inner membrane (NADH dehydrogenase, cytochrome c reductase, and cytochrome c oxidase) perform the transfer and the incremental release of energy is used to pump protons ($H^+$) into the inter-membrane space. This process is efficient, but a small percentage of electrons may prematurely reduce oxygen, forming reactive oxygen species such as superoxide. This can cause oxidative stress in the mitochondria and may contribute to the decline in mitochondrial function associated with the aging process. As the proton concentration increases in the inter-membrane space, a strong electrochemical gradient is established across the inner membrane. The protons can return to the matrix through the ATP synthase complex, and their potential energy is used to synthesize ATP from ADP and inorganic phosphate ($P_i$).

The present invention is generally directed to a method for monitoring exemplary mitochondrial metabolism in response to a potential modulating agent such as an inhibitor, an activator, an uncoupler, and a pathway sidestepping or enhancement agent (collectively referred to as a modulator). When the mitochondria are wired, the electrons can be transferred from Complex IV to the electrode permitting them to be used to reduce oxygen or another redox species at a separate platinum electrode as shown in FIG. 1.

It is noted that direct wiring of mitochondria is preferred but not essential due to the fact that there are many other pathways and electron and cation transporting proteins and molecules that can be exploited through the use of modulators or similar molecules. It will be appreciated by those skilled in the art that any type of electrode suitable for use in the present invention can be used including, but not limited to, gold, platinum, and palladium. Further, any suitable separator can be used with the salt bridge, but situations exist where a salt bridge is not necessary. By intercepting the electrons in this way, the mitochondria's metabolic state can be monitored in real time electrically and, with this technique, one can differentiate the potential and electron flow of the mitochondria, which are all characteristic of particular metabolic states and certain mitochondrial pathways.

Metabolic pathways are series of chemical reactions occurring within a cell. In each pathway, a principal chemical is modified by a series of chemical reactions. Enzymes catalyze these reactions, and often require dietary minerals, vitamins, and other cofactors in order to function properly. Because of the many chemicals, also known as "metabolites" that may be involved. In addition, numerous distinct pathways can co-exist within a cell. This collection of pathways is called the metabolic network. Pathways are important to the maintenance of homeostasis within an organism. Catabolic (breakdown) and Anabolic (synthesis) pathways often work interdependently to create new biomolecules as the final end-products. A metabolic pathway involves the step-by-step modification of an initial molecule to form another product. The resulting product can be used immediately, as the end-product of a metabolic pathway, or to initiate another metabolic pathway, called a flux generating step, or to be stored by the cell. A molecule called a substrate enters a metabolic pathway depending on the needs of the cell and the availability of the substrate. An increase in concentration of anabolic and catabolic intermediates and/or end-products may influence the metabolic rate for that particular pathway.

Each metabolic pathway consists of a series of biochemical reactions that are connected by their intermediates: the products of one reaction are the substrates for subsequent reactions, and so on. Metabolic pathways are often considered to flow in one direction. Although all chemical reactions are technically reversible, conditions in the cell are often such that it is thermodynamically more favorable for flux to flow in one direction of a reaction.

Unique currents and potentials associated with the mitochondria's metabolism of different metabolic substrates such as fatty acids and pyruvate have been found when different classical inhibitors are present. This uniqueness of current, potential, and metabolic energy conversion for each individual inhibitor yields a wealth of information that would be difficult and time consuming to acquire by traditional mitochondrial assay techniques. Because of the analytical nature of electrochemical measurements, very minute changes in mitochondrial metabolism in response to therapeutic levels of drug concentration are possible. This permits large chemical libraries to be tested at many different concentrations to determine if a potential modulating agent has an effect on mitochondrial metabolism of a particular substrate, if it does so at a therapeutic concentration, and what complex or enzyme the compound targets. These data are a powerful tool that can then be used to focus strictly on compounds that show the ability to efficiently target a particular aspect of the mitochondria to treat a particular disease by tuning the mitochondria's metabolism or substrate pathway.

Figure 2:
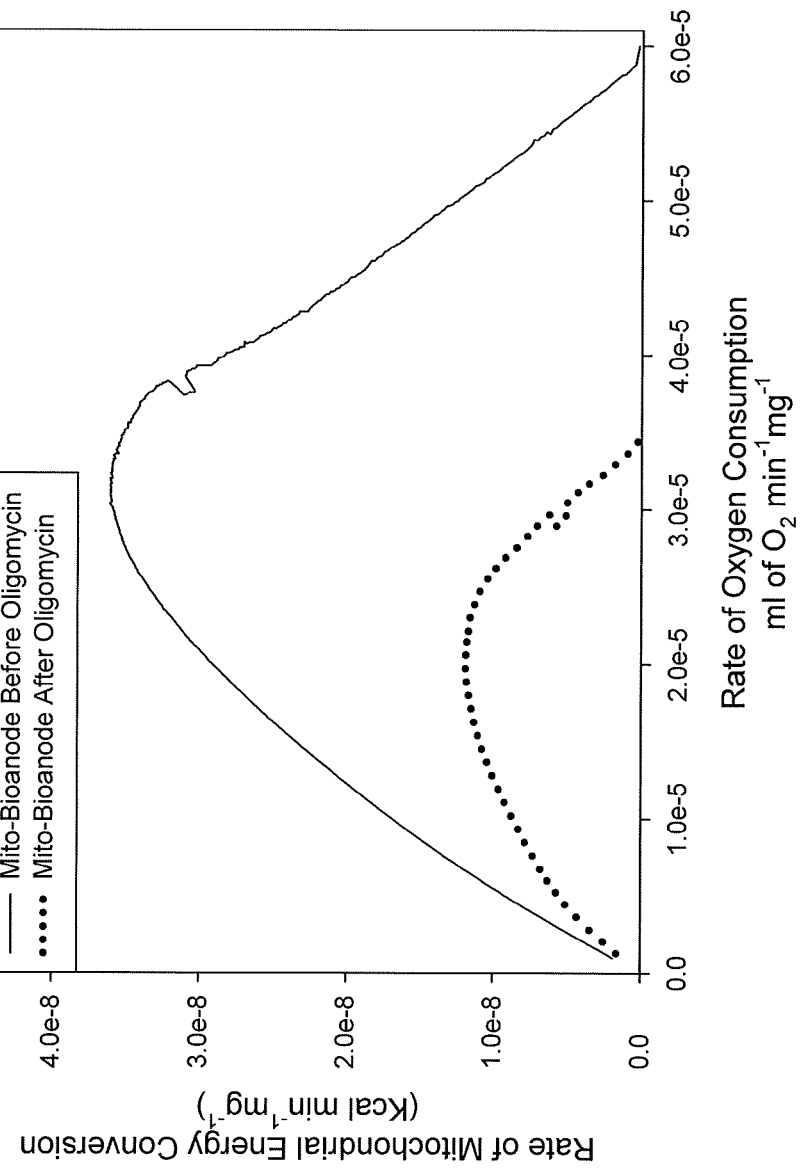
FIG. 2 is a graphical representation of plots for mitochondria bioanodes operating in pyruvate solution coupled with a platinum cathode before (upper line) and after (lower line) treatment with oligomycin in accordance with certain embodiments of the present invention.
Figure 3:
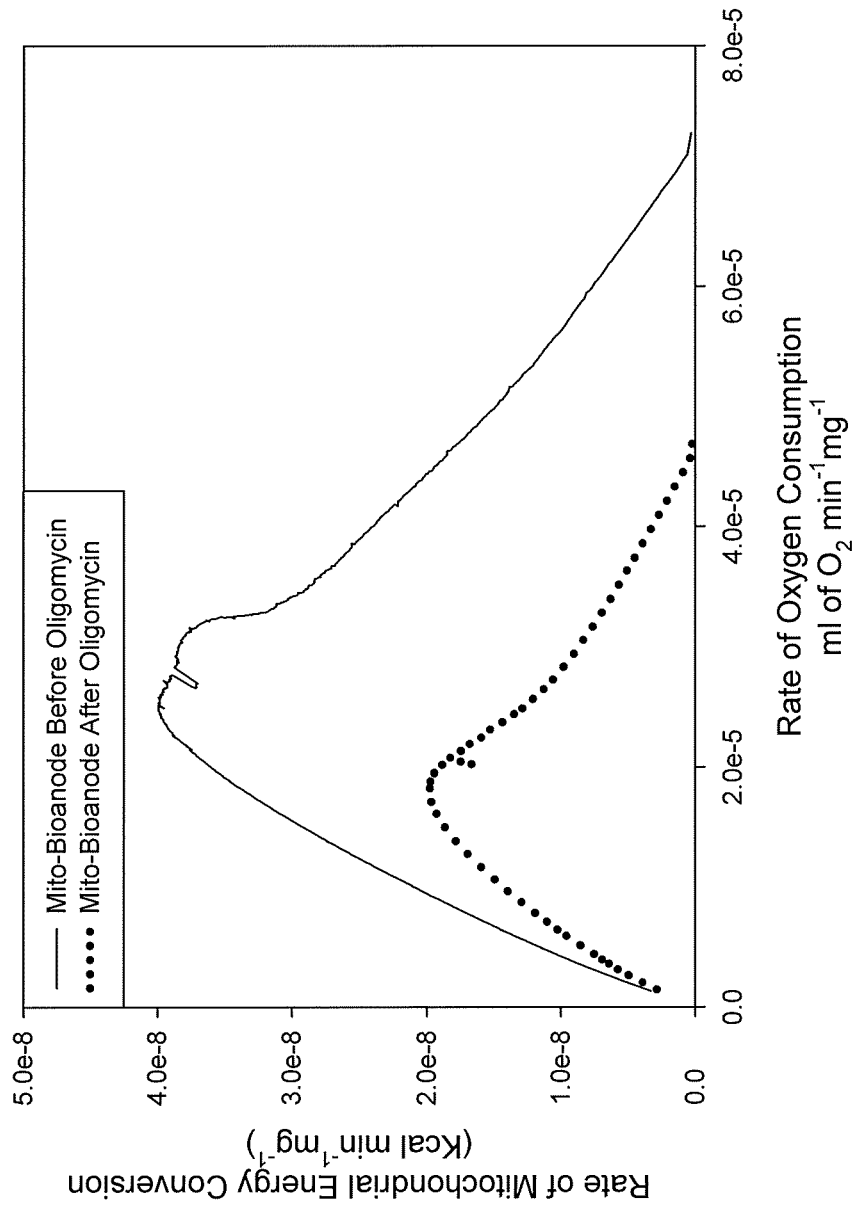
FIG. 3 is a graphical representation of plots for mitochondria bioanodes operating in acetate solution coupled with a platinum cathode before (upper line) and after (lower line) treatment with oligomycin in accordance with certain embodiments of the present invention.
Figure 4:
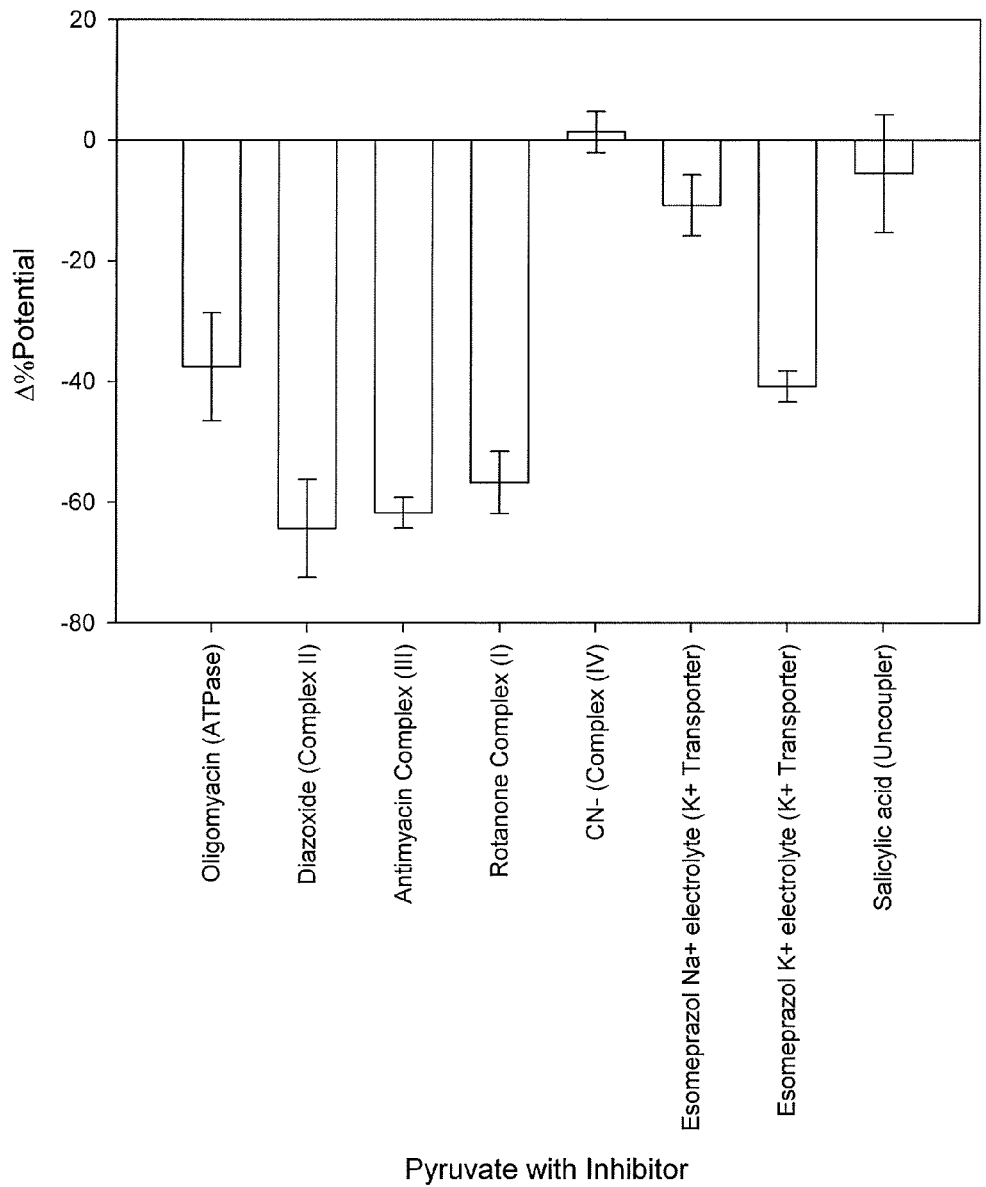
FIG. 4 is a bar chart representation showing percent attenuation of measured open circuit potential with respect to the mitochondria using pyruvate as a metabolic substrate before being exposed to a given inhibitor in accordance with certain embodiments of the present invention.
Figure 5:
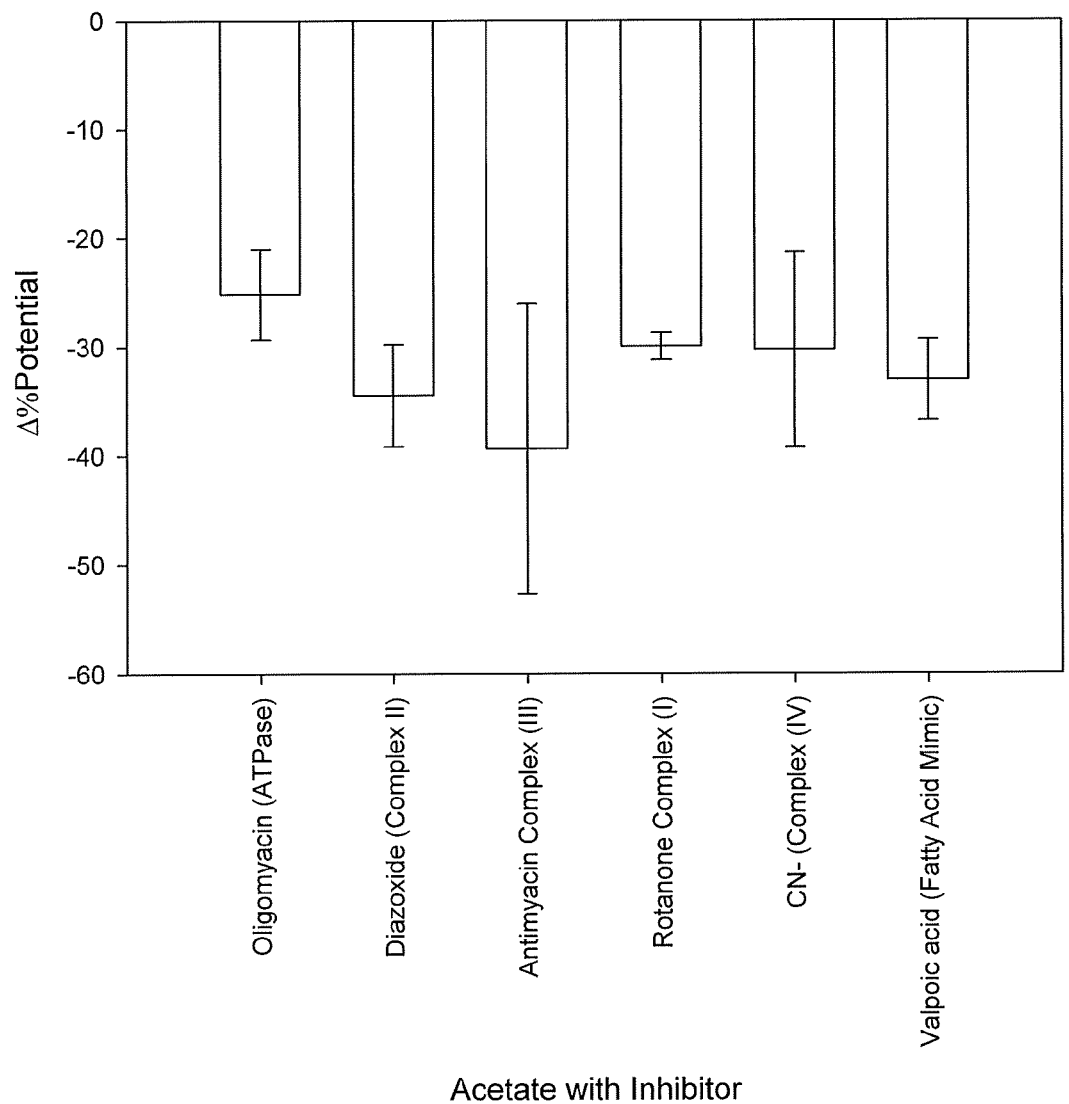
FIG. 5 is a bar chart representation showing percent attenuation of measured open circuit potential with respect to the mitochondria using acetate as a fatty acid metabolic substrate before being exposed to a given inhibitor in accordance with certain embodiments of the present invention.

Monitoring Mitochondrial Function With Respect to Classical Inhibitors. It is found that the attenuation of electrical current (which constitutes part of the metabolic flux and is directly relatable to oxygen consumption or substrate turnover) generated from immobilized mouse liver mitochondria was unique for each inhibitor or mitochondrial active compound with respect to the inhibitors or compounds target as shown in FIG. 2. In addition, it was also found that changing the metabolic substrate, such as pyruvate to a fatty acid, also gave unique attenuation for some of the inhibitors as shown in FIG. 3. Open circuit potential of the combined mitochondrial anode reaction and the oxygen-reducing cathode reaction was also measured before and after the addition of a modulating inhibitor. There was a good correlation between open circuit potential and mitochondrial inhibition for both pyruvate (FIG. 4) as a metabolic substrate and acetate (FIG. 5).

Figure 6:
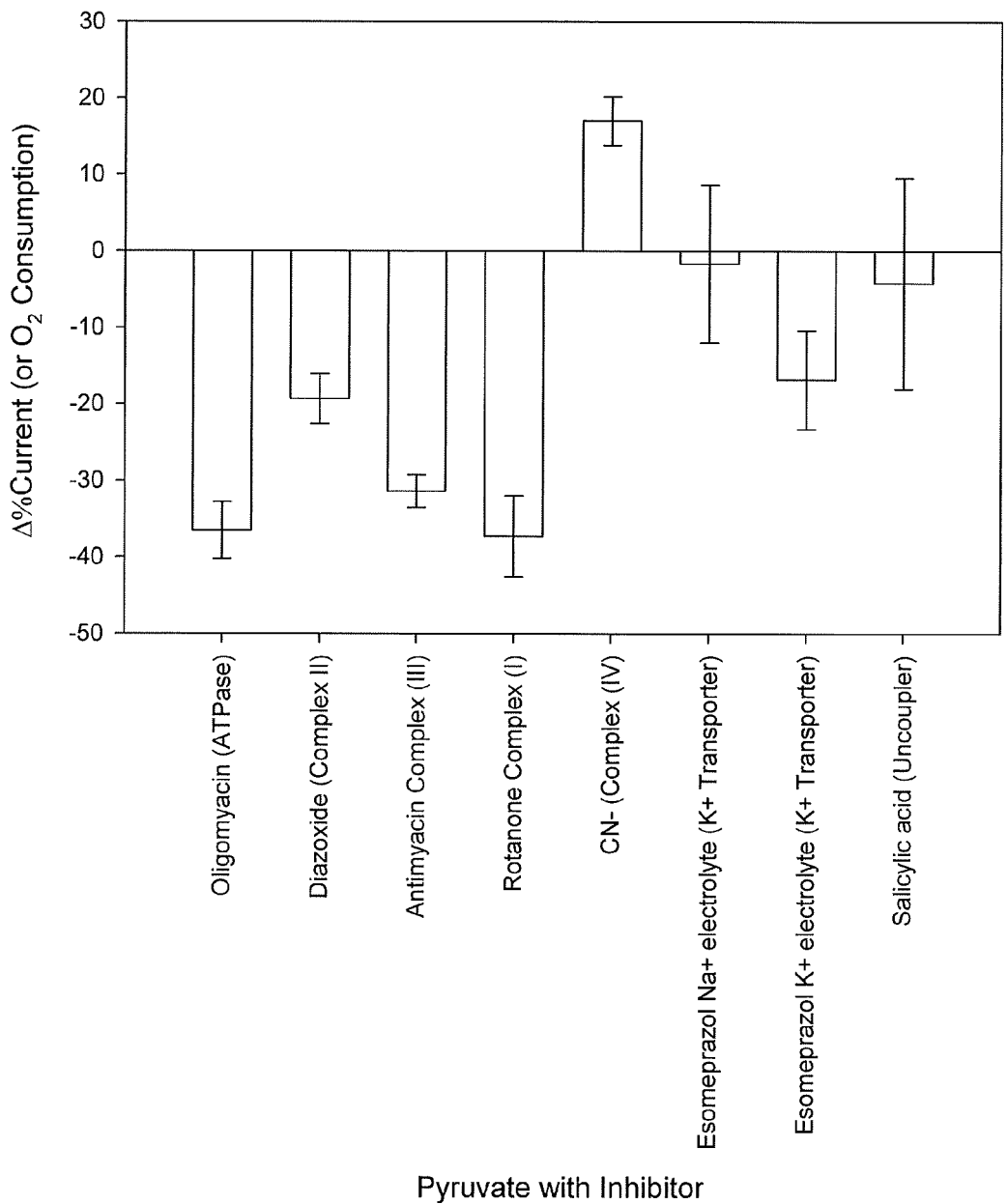
FIG. 6 is a bar chart representation showing percent attenuation of measured electrical current with respect to the mitochondria before the solution was spiked with a given inhibitor in accordance with certain embodiments of the present invention.
Figure 7:
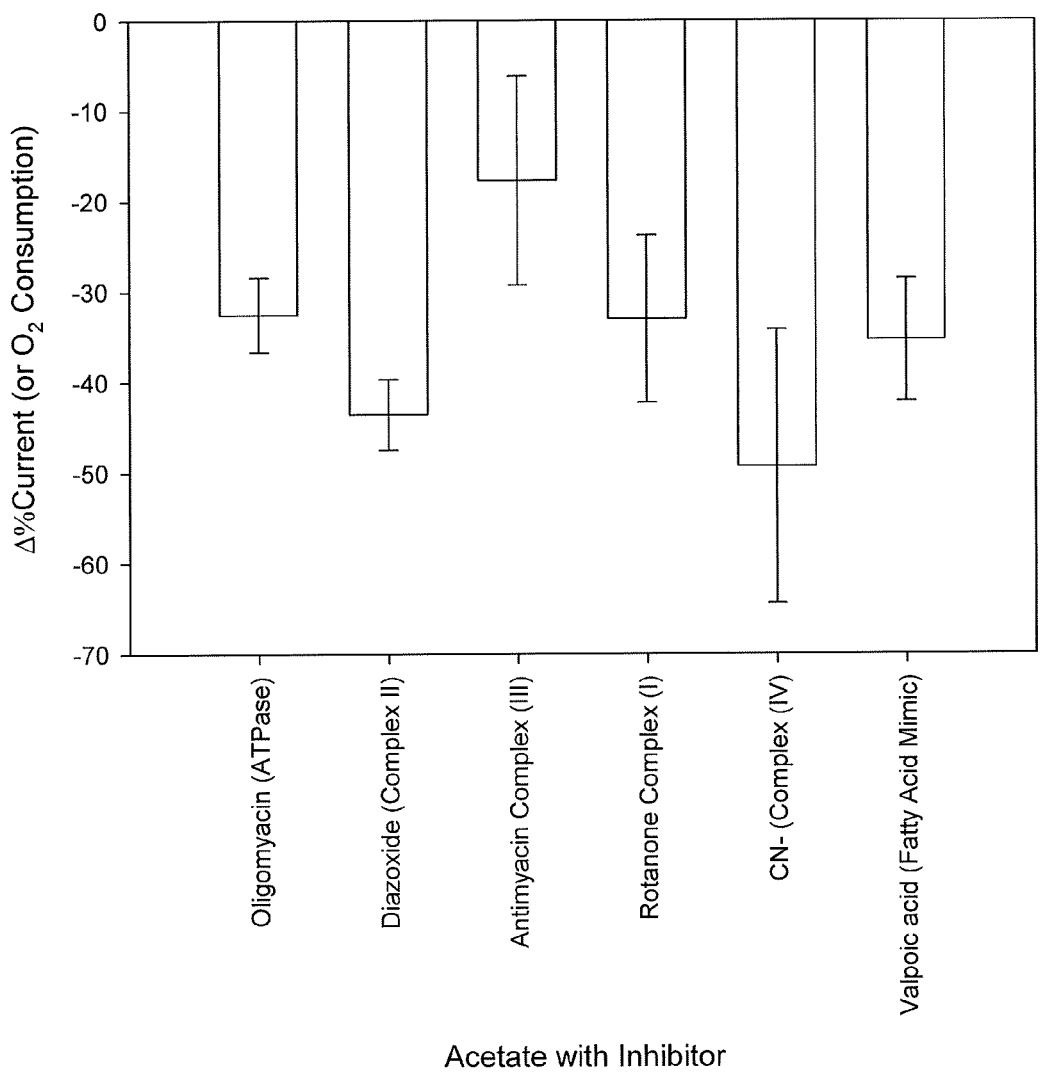
FIG. 7 is a bar chart representation showing percent attenuation in measured electrical current with respect to the mitochondria before the solution was spiked with a given inhibitor in accordance with certain embodiments of the present invention.

Unique current and potential profiles were observed for each combination of inhibitor and metabolic substrate and even electrolyte. Because current is a measurement of the rate of electron flow, and oxygen reduction is a 4-electron process, current measurement permits the direct measurement of oxygen usage as shown in FIGS. 6-7. For example, diazoxide (an inhibitor of Complex II) only demonstrates partial inhibition with pyruvate [Dröse et al., Biochim. Biophys. Acta 1790, 558-565 (2009)] that can be correlated with the partial oxidation of pyruvate in the citric acid cycle because the first one-half of the cycle is still active.

Because this assay system utilizes both an anodic and cathodic reaction, some current is observed even when the mitochondria are nonfunctional at close to short circuit potentials because the cathodic reaction can force a response from the anode, thereby causing oxidative side reactions that do not generate ATP. In this case, the relative oxygen consumption can be plotted versus the energy produced for both pyruvate and fatty acid metabolism with and without inhibitor as shown in FIGS. 2-3. These measurements are greatly affected if one electrode (in this case, the mitochondria-wired anode) is not performing at full capacity, thereby making it easy to show the level of attenuation.

Figure 8:
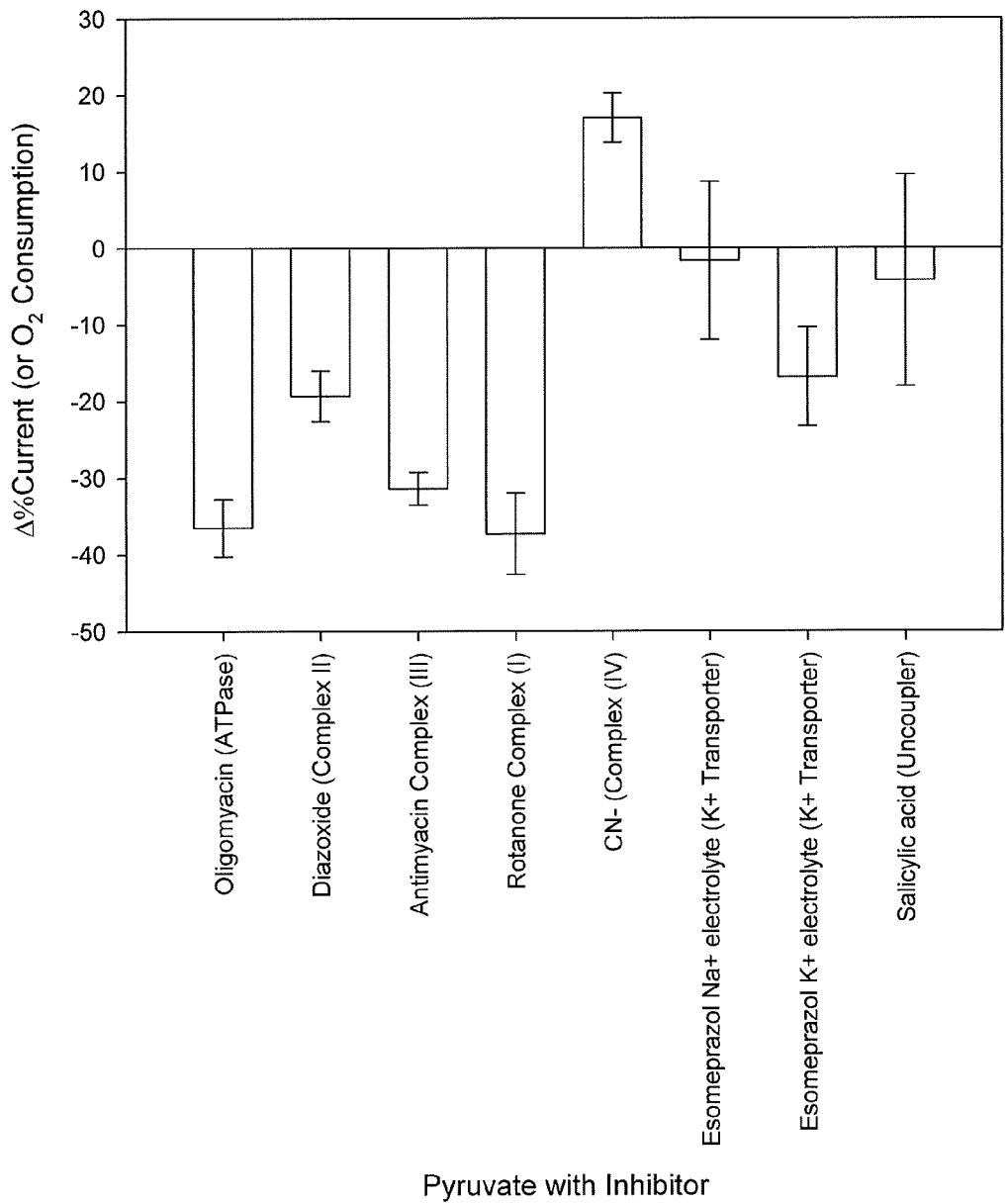
FIG. 8 is a bar chart representation showing percent attenuation of measured metabolic energy conversion with respect to the mitochondria using pyruvate as metabolic substrate before being exposed to a given inhibitor in accordance with certain embodiments of the present invention.

These plots form curves where maximum useful energy conversion (rate of energy from the mitochondrial metabolism) occurs at the top of the arch and then decreases as cathodic reaction forces oxidative side reactions at the anode to occur at high electron flows. Even so, the maximum current and open circuit potential measurements are still very useful and can yield clues as to what is occurring to the mitochondria. For this system operating on pyruvate, 82.2±2.4% attenuation in energy was considered to be complete inhibition of the mitochondrial function, and any inhibitor that gave less attenuation than this value was considered to only partially inhibit mitochondrial function as shown in FIG. 8.

Both rotenone and antimycin demonstrated this strong inhibitory response. From a fundamental point of view, if electron transport chain Complex I or Complex III are nonfunctional, it is difficult to shuffle electrons to the electrode. If Complex I is completely inhibited, any further metabolic reactions do not occur, thereby resulting in no electrons being transported through the electron transport chain. If Complex III is inhibited, electrons cannot pass beyond that point resulting in the same effect. The only difference between the effect on the mitochondria is that, when Complex III is inhibited, the mitochondria can metabolize until all of their cofactors such as NAD+ and ubiquinone are reduced but, when Complex I is inhibited, the coenzymes are all fully oxidized.

Complex II inhibition demonstrates only partial inhibition with 65.2±1.5% attenuation in energy conversion because Complex I and Complex III still permit NADH to have its electrons shuffle through the electron transport chain. The reason we more inhibition (65%) is seen instead of one-half inhibition (41%), even though one-half of the citric acid cycle is still active, is due to the fact that there is product inhibition occurring because succinate levels build up when Complex II is inhibited.

Complex IV, when inhibited with $CN^-$, showed no change in potential and actually increased current. This result occurs because mitochondrial oxygen reduction is not relied upon to monitor metabolism due the fact that oxygen is reduced on a separate electrode so that if large quantities of oxygen are present, oxygen reduction is actually a competitive process to the measurements. Thus, increased current is seen because competition for the electron is eliminated. However, in classical metabolic assays that measure ATP synthesis, the only information yielded is that no ATP is being produced and that the mechanism of how $CN^-$ inhibits metabolism is not detailed. Using the present invention, therefore, not only can potential drug candidates be screened, but their mechanism of action can be pinpointed as well without having to undertake other tedious studies.

Inhibition of the ATPase with oligomycin showed 60.9±1.0% attenuation in energy conversion and 36.5±3.7% decrease in current. Whereas the overall energy conversion was decreased dramatically, there was still less of an inhibition of metabolism than what one would expect because oligomycin does not permit protons to be transported even though the rest of the mitochondrial metabolic processes are functioning until they stop due to overpolarization and full reduction of the coenzymes. This phenomenon is seen because the mitochondria have a small amount of protons that can leak out of the membrane and do not end up generating ATP, but can be measured with this technique nonetheless because it measures electron flow that is accompanied by even the leaked protons and not ATP or membrane potential like other techniques.

Esomeprazole, a selective $K^+$ pump inhibitor, was tested using pyruvate as metabolic substrate in both a sodium chloride electrolyte and a potassium chloride electrolyte. The attenuation of the treated mitochondria's metabolism was different when operated with both $Na^+$ and $K^+$ electrolyte. The attenuated current for $Na^+$ was 1.7±10.3% and 16.8±6.4% for $K^+$. These were not statistically significant results; however, the difference in metabolic energy production for $Na^+$ was 19.9±7.6% and 58.8±11.1% for $K^+$, which was statistically significant.

These results demonstrate that esomeprazole's effect is more pronounced in a solution that contains potassium ions where they need to be transported for charge balance, but this effect is lessened when only sodium ions are present in solution, thereby indicating that, while esomeprazole may be strongly inhibitory to $K^+$ transport, it is also mildly inhibitory to the $Na^+$ transport as well and further indicating that esomeprazole may have other more subtle mechanisms of action that are not easily seen with traditional biochemical techniques.

Salicylic acid, a mitochondrial uncoupler, was tested using pyruvate as metabolic substrate to determine the electrode characteristics of uncoupled mitochondria. The currents of the salicylic acid-treated mitochondria were not statistically significant compared to the mitochondria before they were treated. However, the treated mitochondria did show that the uncoupling permitted them to generate 18.6±1.5% higher metabolic energy flux than mitochondria that where untreated.

Figure 9:
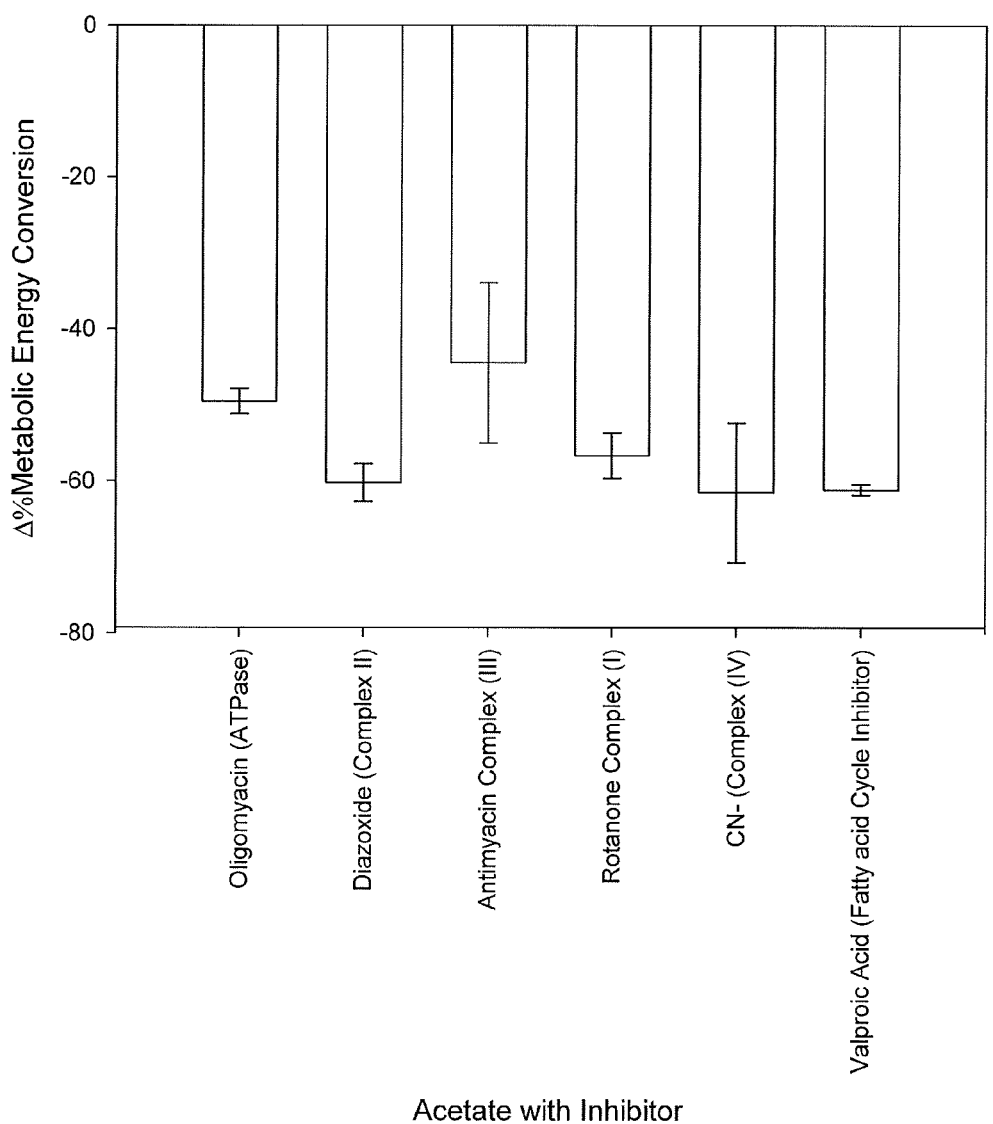
FIG. 9 is a bar chart representation showing percent attenuation of measured metabolic energy conversion with respect to the mitochondria using acetate as a fatty acid metabolic substrate before being exposed to a given inhibitor in accordance with certain embodiments of the present invention.
Figure 10:
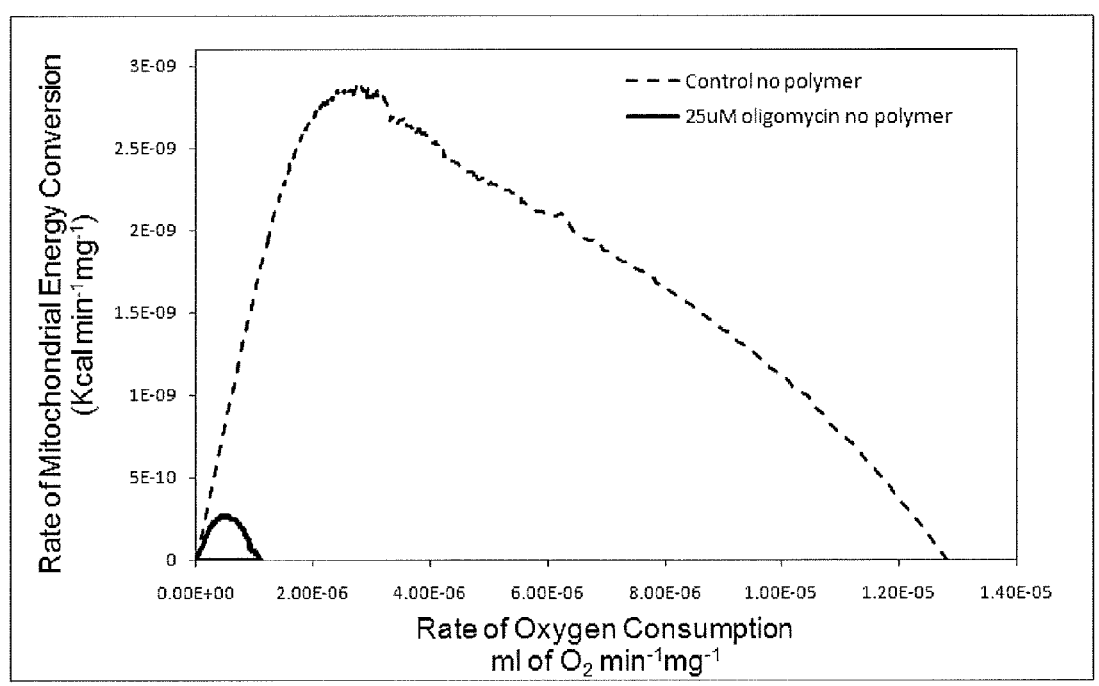
FIG. 10 is a graphical representation of plots for mitochondria bioanodes (in the absence of the polymer layer) operating in pyruvate solution coupled with a platinum cathode before (upper line) and after (lower line) treatment with oligomycin in accordance with certain embodiments of the present invention.
Figure 11A:
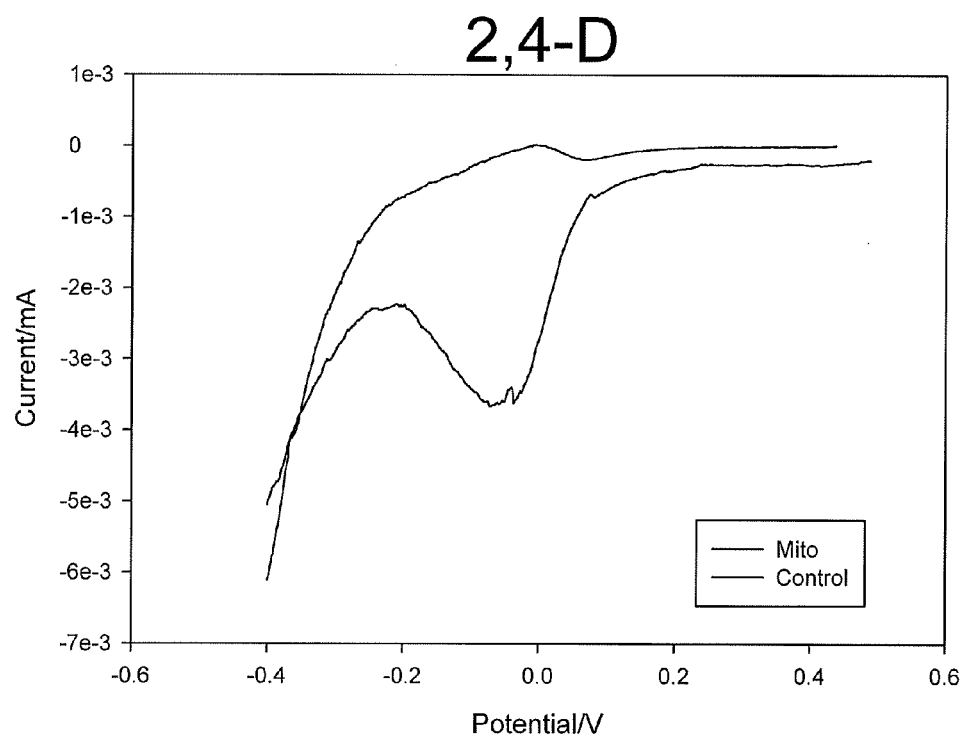
FIG. 11 is a bar chart representation of potato mitochondria.
Figure 11B:
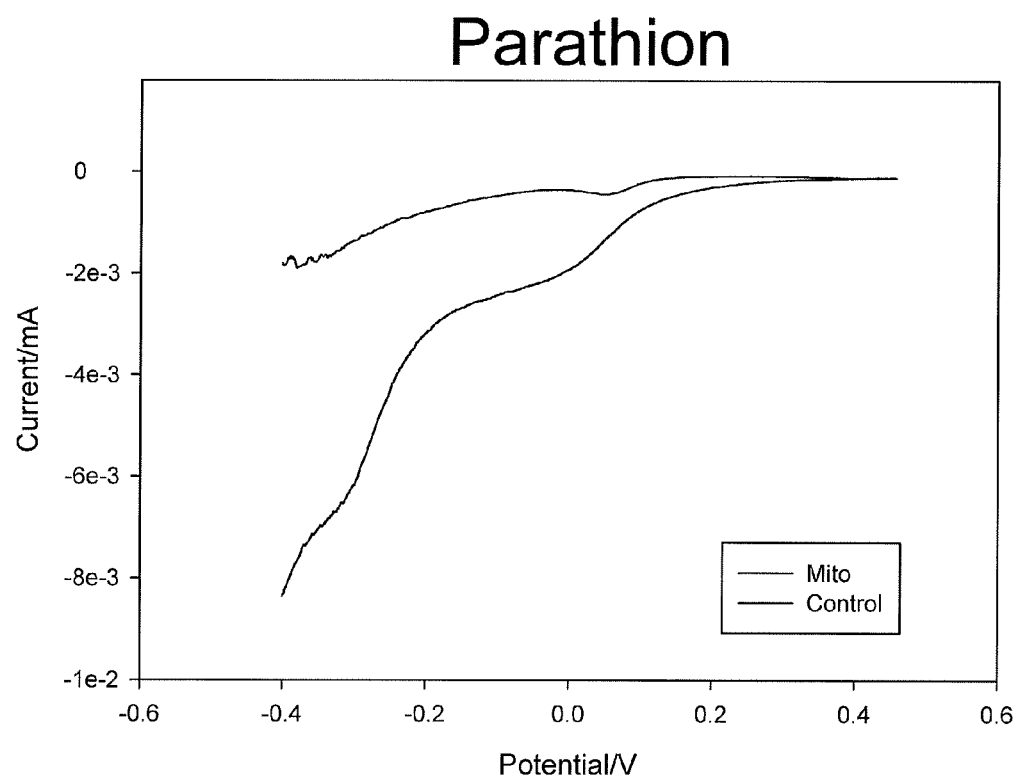
Figure 11C:
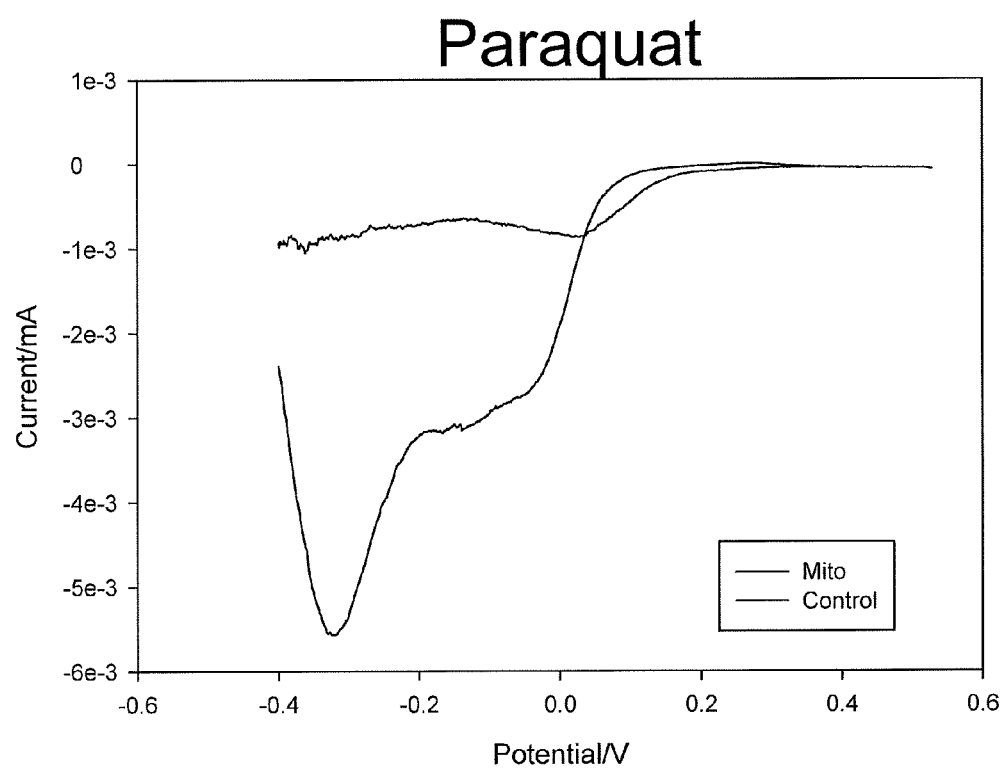
Figure 11D:
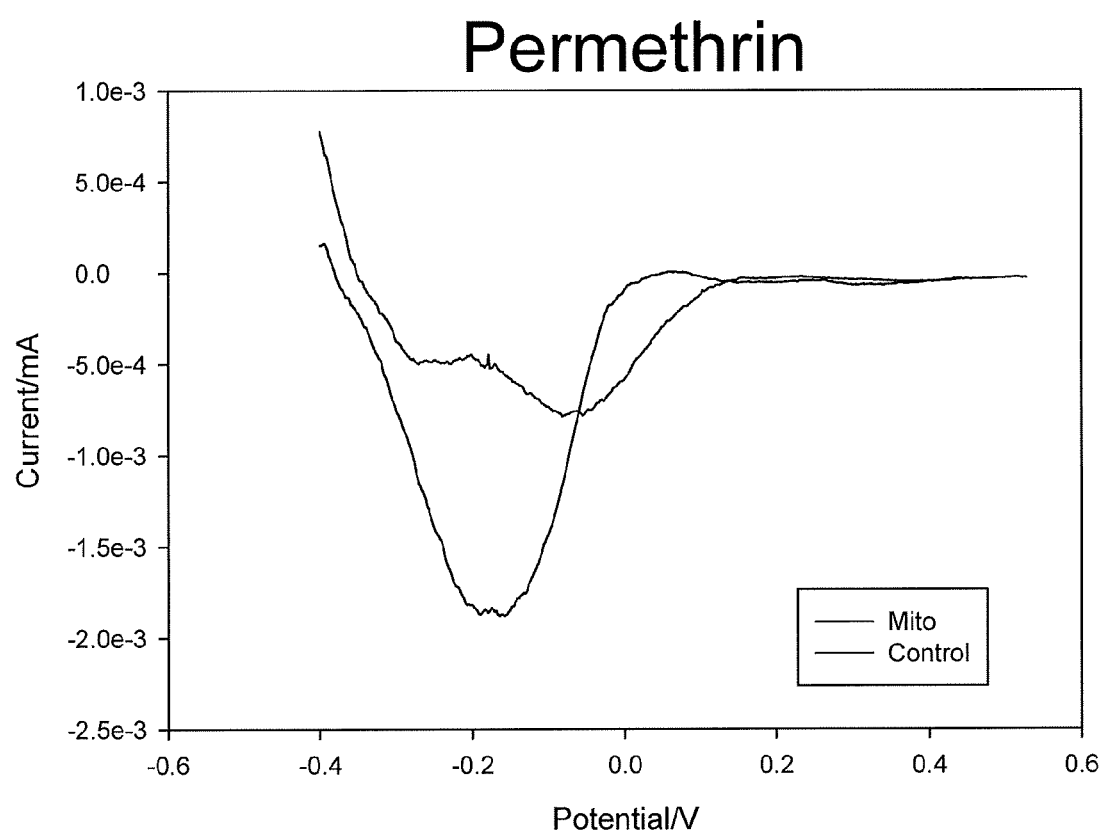
Figure 11E:
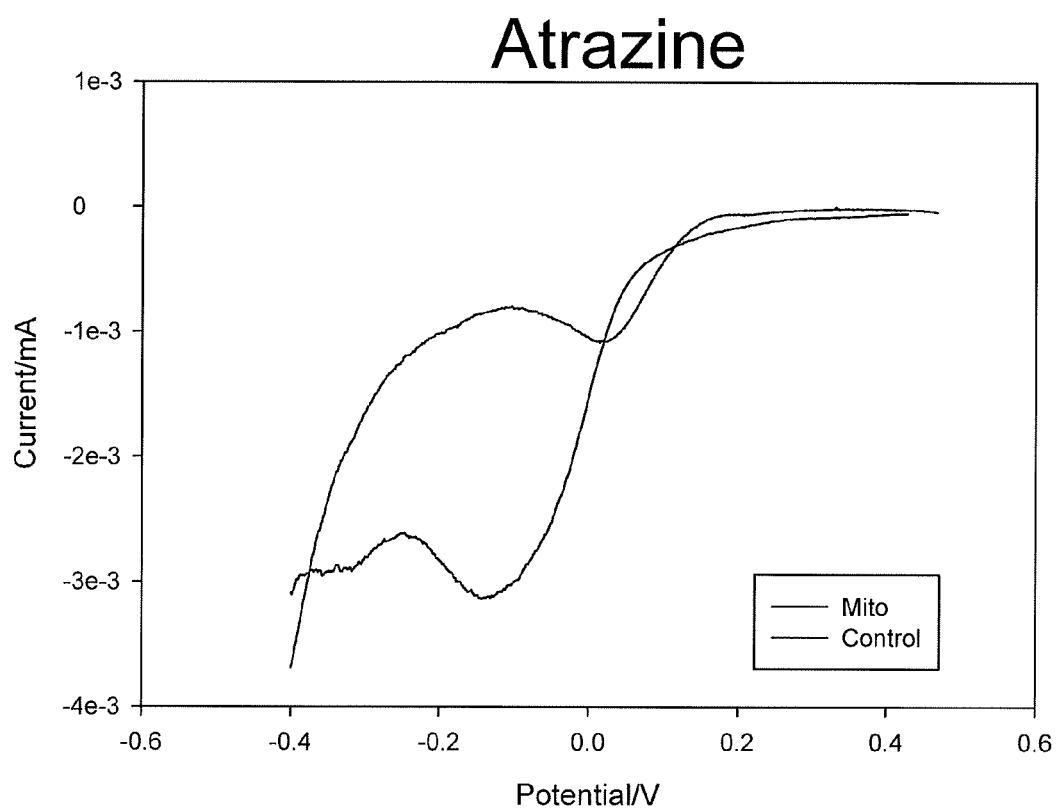

Comparing Pyruvate Metabolism to Fatty Acid Metabolism. Mitochondria that used acetate, a fatty acid, as metabolic substrate were also assayed to determine what the effect would be from forcing the mitochondria to operate solely on a fatty acid as a metabolic substrate, while examining the metabolic attenuation of the mitochondria after the classical inhibitors were added as shown in FIG. 9. Because the fatty acid pathway is different for the first portion of its metabolism, one of the inhibitors used was valproic acid, a double chain fatty acid that inhibits the fatty acid oxidation to acetyl CoA, which is then fed into the citric acid cycle. The mitochondria operating on acetate substrate all demonstrated very similar attenuation in current and energy to the pyruvate metabolizing system except, in all of the results, there was noticeably less change and higher standard deviations indicating that acetate may be affecting some other function of the mitochondria that pyruvate was not.

EXAMPLES

Mitochondrial extraction. Mitochondria were isolated from mouse liver and suspended in phosphate buffer at a concentration of 18.6 mg/ml. Before use, 1 mg/ml of ADP was added to the solution. Mitochondria are obtained as described in Arechederra et al., *Electrochim. Acta* 53, 6698-6703 (2008); Germain et al., *J. Am. Chem. Soc.* 130, 15272-15273 (2008); Arechederra et al., *Electrochimica Acta* 54, 7268-7273 (2009); and Addo et al., *Electroanalysis*, 22, 807-812 (2010), and the citations therein. Kits are also commercially available (Sigma-Aldrich No. MITOISIO1-1KT) for preparation of mitochondria from animal cells. Kits are similarly commercially available for the preparation of mitochondria from yeast cells such as *Saccharomyces cerevisiae, Pichia pastoris*, and *Schizosaccharomyces pombe* (Sigma-Aldrich No. MITOISO3-1KT).

According to the electrochemical assay these mitos showed the best results in biofuel cells when used for carbon capture or for screening drugs specific for mitochondrial carbonic anhydrase. If demand for mitochoindria increases for biofuel-cell applications, an alternative source of mitochondria is needed. Since we have used mitochondria from yeast which worked, her group purified mitochondria from potato-tuber.

Preparation of Plant Mitochondria

Unlike mammalian tissue, plant tissues contain a relatively high concentration of phenolic material, and phenol oxidases that catalyze the conversion of phenols to quinones. Refer to FIG. 11. Quinones or tannins can form a complex with a mitochondrion and inactivate the mitochondrial function. To avoid this complication, several precautions were followed during plant mitochondrial purification that are described below using potato mitochondria as exemplary. Previous uses of potato mitochondria are discussed in US Publication No. 20090305089. Mitochondria obtained from that preparation provided electrodes inferior to those prepared as discussed below.

1. Potato skins were removed taking out a small portion of tuber flesh, because skin contains most of tannins and quinones.

2. The tuber was cut in thin slices and soaked in ice cold PBS containing 2 mM metabisulfite and cysteine each for 20 minutes to inactivate the remaining quinones and tannins.

3. Tuber slices were soaked and washed twice to remove the majority of starch granules that also have a deleterious effect on mitochondrial function.

The remaining procedures are similar to the stepwise sucrose-gradient procedure used for isolation of mouse-liver mitochondria as discussed in Nagao et al., *Proc. Natl. Acad. Sci. USA* 90, 7623-7627 (1993) and Nagao et al., *Proc. Natl. Acad. Sci. USA* 91, 10330-10334 (1994).

Preparation Procedure:

Tuber slices were washed with PBS containing 2 mM of cysteine and 2 mM of sodium metabisulfite ($Na_2S_2O_5$) twice at 4° C.;

Slices were homogenized in homogenizing buffer: 0.3 M sucrose, 1.4 mM Tris-EDTA pH 7.5 containing 1 mM each of PMSF, benzamidine, iodoacetamide, 1 mg/ml BSA and 1 µM cysteine and metabisulfite using volume ratio of buffer to tuber 4:1;

Homogenization was carried out using Polytron™ at high speed and the homogenate was kept on ice during homogenization;

For complete homogenization, polytron-homogenization was repeated three times, 5-10 minutes each;

Large chunks were removed by centrifugation at 600×g for 15 minutes; centrifugation being repeated twice;

Mitochondria were isolated by centrifugation at 10000×g for 20 minutes. The mitochondrial pellet was saved and suspended in PBS containing PMSF, bezamidine and EDTA, 1 mM of each;

Protein concentration of the mitochondrial preparation was determined, and usually found to be about 20-22 mg from 300 g of tuber;

This procedure yields about 0.007 percent of mitochondria with respect to total tuber mass.

Energy production was not quite as good as the best from mouse mitochondria made, but results were favorable, providing a scalable, commercial preparation.

Experimental Protocol for Pesticide Toxicity Sensing

Materials

Yeast extract and DL-Lactic acid; Nafion and paraquat and all other reagents used can be obtained. Solutions can be prepared with de-ionized water.

Yeast Cultivation

Lactate media can prepared by following the protocol outlined by Leister and Johannes (Leister D, Johannes M H, eds. *Mitochondria: Practical Protocols*). *Saccharomyces cerevisiae* cells can be inoculated into the media and allowed to grow for approximately 3 days. Cells were collected by centrifugation.

Mitochondria Extraction

Mitochondria can be isolated from the cultivated *Saccharomyces cerevisiae* by differential centrifugation [1]. The cell pellet can be first rinsed with distilled water, then suspended in Tris-$SO_4$ buffer and incubated for 10 min at 30° C. under agitation (~140 rpm). The cells can be collected by centrifugation and re-suspended in sorbitol buffer. Lyticase (2 mg/10 g cells) can be added and the suspension can be again incubated under agitation for 40 min until spheroplasts formed. From this point on, all steps can be performed with ice cold buffers, and centrifugation was performed at 4° C. The spheroplasts can be harvested and re-suspended in sorbitol buffer. After centrifugation, they can be suspended in a 0.6M sorbitol buffer containing 20 mM HEPES-KOH and 1 mM PMSF, transferred to a Dounce homogenizer, and homogenized with 15-20 strokes.

The homogenate can be centrifuged and the supernatant kept. This homogenization process can be repeated once more, and the supernatants can be combined and centrifuged at 12,000 g for 10 min. The pellet can be re-suspended in another 0.6M sorbitol buffer which contained 20 mM HEPES-KOH only, and centrifuged at 2,000 g for 5 min to remove any remaining cell debris. The supernatant can be transferred to a fresh tube and centrifuged at 12,000 g for 10 min. The remaining pellet can be a light brown and contained the isolated mitochondria.

Preparation of Modified Nafion

The immobilization membrane can be prepared as previously described in the literature {T. J. Thomas, K. E. Ponnusamy, N. M. Chang, K. Galmore, S. D. Minteer, Journal of Membrane Science 213 (2003) 55; C. M. Moore, N. L. Akers, A. D. Hill, Z. C. Johnson, S. D. Minteer, Biomacromolecules 5 (2004) 1241; C. M. Moore, S. Hackman, T. Brennan, S. D. Minteer, Journal of Membrane Science 255 (2005) 233; T. L. Klotzbach, M. M. Watt, Y. Ansari, S. D. Minteer, Journal of Membrane Science 282 (2006) 276; and R. L. Arechederra, et al. Electrochimica Acta 54 (2009) 7269}

First, 2 ml of a 5% by wt. Nafion solution and an excess of tetrabutylammonium bromide (TBAB) were mixture-cast into a weigh boat. The mixture can be allowed to dry in a low-humidity environment overnight. Excess salt can be removed by soaking overnight in 18 MΩ water followed by triple rinsing and air drying. The resulting membrane can be then re-suspended in ethanol.

Immobilization of Mitochondria on Toray Paper

The wet mitochondria pellet can be used directly. The wet pellet (100 mg) can be suspended in 100 µL of a pH 8.0 homogenization buffer containing 2.6M NaCl, 50 mM EDTA, 100 mM Trizma® Base, 28 mM DTT, and 0.1% cysteine [6]. Then, 2.5 mg ADP can be added to the suspension, followed by the addition of 100 µL of the TBAB-modified Nafion suspension, and the resulting suspension can be mixed on a vortex mixer for 10 s. Immediately, 50 µL of this suspension can be pipetted onto 1 $cm^2$ pieces of unmodified Toray paper (E-Tek, Somerset, N.J.) and allowed to dry under a fan for 15-20 min. The electrodes can be then immersed in separate glass vials, each containing 5 mL of pH 8.0 phosphate buffer that contained 1 mg/mL ADP, 500 mM NaCl, and 100 mM sodium pyruvate, and allowed to soak overnight at 4° C. Control electrodes can be prepared in the same way, except they contained no mitochondria.

Electrochemical Measurements

The electrochemical test cell can be fabricated as in Arechederra et al [7]. An air-breathing cathode can consist of Nafion 212 hot pressed to a gas permeable ELAT electrode with 20% Pt on Vulcan XC-72. The fuel solution used was a 100 mM phosphate buffer (pH 8.0) which contained 1 mg/mL ADP, 1M $NaNO_3$, and 100 mM sodium pyruvate. This solution can be poured into the anodic chamber of the cell, and the 1 $cm^2$ part of the bioanode was immersed in it. The cell can then connected to a CH Instruments Model 700A potentiostat and the open circuit potential (OCP) can measured. Linear sweep voltammetry (LSV) can be then performed, starting at the OCP and scanning to −0.4V at a scan rate of 1 mV/s.

Pesticide Studies

After the initial electrochemical measurements, the bioanode was placed in a glass vial containing 5 mL of a pesticide solution and soaked overnight at 4° C. Again, the OCP and LSV were measured with the bioanode immersed in fuel solution. Five pesticides were tested in this study: 2,4-D, Parathion, Paraquat, Permethrin, and Atrazine. They were tested at concentrations of 0.7 mg/L, 10 mg/L, 12.2 mg/L, saturated, and 5 mg/L, respectively.

Results and Discussion

As shown in the voltammograms in the Powerpoint slide, the mitochondrial modified electrodes were capable of sensing the presence of all five pesticides, showing that pesticides do indeed affect electrochemical performance. Table 1 shows the quantitative difference in peak current and peak area before and after inhibition with the pesticides.

TABLE 1

Average and standard deviation for peak potential before inhibition by pesticide (Ep), change in peak height ($\Delta$ip), and change in peak area ($\Delta$Ah) are shown. Number of electrodes tested for each pesticide are as follows: 2,4-Dichlorophenoxyacetic acid (n = 4); Parathion (n = 4); Paraquat (n = 5); Permethrin (n = 5); Atrazine (n = 4).

| Pesticide | Ep/V | $\Delta$ip/A | $\Delta$Ah/C |
|---|---|---|---|
| 2,4-D | −0.024 ± 0.014 | −1.617E−06 ± 5.286E−07 | −8.237E−05 ± 1.713E−05 |
| Parathion | −0.037 ± 0.015 | −4.491E−07 ± 2.512E−07 | −2.721E−05 ± 9.349E−06 |
| Paraquat | −0.062 ± 0.010 | −8.582E−07 ± 1.870E−07 | −3.690E−05 ± 1.109E−05 |
| Permethrin | −0.181 ± 0.013 | −1.015E−06 ± 2.065E−07 | −6.597E−05 ± 1.238E−05 |
| Atrazine | −0.122 ± 0.037 | −8.290E−07 ± 2.197E−07 | −6.809E−05 ± 1.708E−05 |

Immobilization of mitochondria onto electrodes. To a vial 5.0 mg of COOH-modified multiwalled carbon nanotubes (OD 30-50 nm) (L 1-10 µm) (COOH-MWCNT) were added. Then 50 µl of ethanol was added to this vial, and was permitted to be absorbed by the nanotubes. Thereafter, 100 µl of deionized water was added to the same vial, and the vial was capped and placed into a sonic water bath for 30 minutes to disperse the nanotubes.

Once the nanotubes were dispersed, the vial was placed in an ice bath to chill. Once chilled, 100 µl of mouse mitochondria suspension 18.6 mg/ml was added and the vial was vortexed for 5-10 seconds. Immediately following the mixing, the mitochondria/MWCNT suspension was pipetted onto cleaned and polished glassy carbon electrodes, 10 µl/0.07 cm2. Once the solution had evaporated from the electrode after 10 minutes, 1.5 µl/0.07 cm2 of neutralized ionomer suspension was pipetted on top and then allowed to soak in and dry. Once dry, the electrodes were placed into a substrate solution for 1 hour that contained 100 mM pyruvate (or 100 mM acetate), 1 mg/ml ADP, 100 mM NaCl electrolyte (or 100 mM KCl electrolyte for esomepazole), and 10 mM phosphate buffer pH 7.50. After soaking for 1 hour, the electrodes were tested.

Inhibition of mitochondrial electrodes. After the mitochondria modified electrodes were tested, they were soaked for 1 hour in substrate solution that contained a given inhibitor and then tested again. The concentration for oligomycin was 47.5 µM, rotenone 0.5 µM, diazoxide 1.0 mM, antimycin 18.0 µM, esomeprazole 216.0 µM, CN⁻ 1.0 µM, salicylic acid 1.0 µM, valproic acid 1 mM.

Experimental setup. The mitochondria-modified electrodes (anode) were placed into beaker containing the respective substrate solution that they were soaked in, along with a platinum mesh cathode that was separated by a commercially available Nafion® NRE212 membrane that served as an ion selective salt bridge. The cathode compartment of the cell contained 10 mM pH 7.50 phosphate buffer with 100 mM NaNO3 electrolyte. The anode and cathode were connected to a CH Instruments model 810 potentiostat interfaced to a PC for electrochemical measurements. Each mitochondria-modified electrode was permitted to reach maximum open circuit potential before performing a linear sweep voltammogram that started at the cells open circuit potential and ended at 0.000V at a rate of 1.0 mV per second.

Mitochondria modified electrodes can be fabricated by the following procedure.

To a vial, 5.0 mg of COOH-modified multiwalled carbon nanotubes (OD 30-50 nm) (L 1-10 µm) (COOH-MWCNT) were added. Then 50 µl of ethanol was added to this vial and allowed to be absorbed by the nanotubes. To the same vial, 100 µl of deionized water was added and the vial was capped and placed into a sonic water bath for 30 minutes to disperse the nanotubes. Once dispersed, the vial was placed in an ice bath to chill. Once chilled, 150 µl of mouse mitochondria suspension (18.6 mg/ml) was added along with 0.5 mg adenosine diphosphate and the vial was placed on a vortex mixer for 5-10 seconds. Immediately following the mixing, the mitochondria/MWCNT suspension was coated onto clean carbon electrodes at a loading of 100 µl/cm². The electrodes were allowed to dry completely, then the electrodes were placed into an incubation solution for 1 hour that contained 100 mM pyruvate, 1 mg/ml adenosine diphosphate, 100 mM NaNO₃ electrolyte and 10 mM phosphate buffer pH 8.00. The electrodes were tested in fresh incubation solution using the same electrochemical procedure discussed below. Following these tests, the electrodes were placed into fresh incubation solution that contained a classic mitochondrial inhibitor oligomycin, and allowed to incubate for another hour. After the incubation period the electrodes were tested again, but with fresh oligomycin containing solution.

Two high throughput drug screening assays are contemplated that include: (1) an in vitro non-human and non-animal assay for screening potentially active compounds for causing mitochondrial dysfunction, which is currently done by animal testing further down the drug development pathway—this assay permits one to test drug or mitochondrial active compound candidates for mitochondrial toxicity at an earlier stage and more inexpensively; and (2) a quantitative determination of effects of a mitochondrial drug or active compound on metabolism.

In addition, this technique also permits synergistic compounds to be examined, where one compound alone may or may not have an effect, but when used in addition to another compound provides an enhanced effect or entirely different effect, or a return to normal function. In certain embodiments, the present invention can also be used in connection with water treatment and testing as well as treatment of and testing for biological agents including but not limited to pesticides, herbicides, antibiotics, hormones, poisons, warfare agents, and environmental contaminants that affect organelles such as mitochondria.

One embodiment of the method for monitoring the metabolic state of an organelle in the presence of a potential organelle modulating agent includes providing at least an organelle-modified bioelectrode that is electrically coupled to a second electrode of opposite polarity in a circuit. The method further includes contacting said bioelectrode with an aqueous carrier that contains a biologically acceptable electrolyte thereby providing a portion of the circuit, an effective amount of a potential organelle modulating agent and an effective amount of an organelle substrate. This embodiment also includes reacting the substrate of said carrier at the bioelectrode to form an ionic product that is released into the aqueous carrier-containing electrolyte to thereby provide a current at the second electrode when the circuit is closed. Using one or both of said electrodes to obtain a metabolic flux data set during said reaction can be implemented.

Comparing those data to a control metabolic flux data set obtained under the same conditions in the absence of the potential organelle modulating agent, can thereby be used to determine the metabolic state of the organelle in the presence of the potential organelle modulating agent. The organelle can be any one of a mitochondrion, a mitoplast, a chloroplast, a thylakoid, and a combination thereof and more particularly can be a mitochondria.

The mitochondrion can be from an animal cell, a plant cell, or a fungal cell. The bioelectrode can include a material selected from carbon-based material, a metallic conductor, a semiconductor, a metal oxide, a modified conductor, and combinations thereof. The bioelectrode including a carbon-based material can be from the group consisting of carbon cloth, carbon paper, carbon screen printed electrode, carbon black, carbon powder, carbon fiber, single-walled carbon nanotube, double-walled carbon nanotube, multi-walled carbon nanotube, carbon nanotube array, diamond-coated conductor, glass carbon, mesoporous carbon, graphite, uncompressed graphite worms, delaminated purified flake graphite, high performance graphite, highly ordered pyrolytic graphite, polycrystalline graphite, amorphous carbon, an allotrope of carbon or modified allotrope of carbon, an organic conductive polymer, a redox polymer, a polymer composite, and a combination thereof. The substrate can be selected from the group consisting of a $C_2$-$C_{24}$ fatty acid, a mono-, di- or triglyceride of said $C_2$-$C_{24}$ fatty acid or a mixture thereof, an amino acid, ammonia, urea, an amine compound, lactate, pyruvate, acetyl-CoA, malate, fumarate, succinate, oxaloacetate, ketoglutarate, flavin, ATP, NADH, NADPH, hydrogen, a cytochrome, oxygen, a mono- or disaccharide, and a combination thereof.

Another embodiment of a method for monitoring the metabolic state of an organelle includes electrically coupling an organelle-modified bio-electrode to an electrode having opposite polarity by contacting an aqueous carrier between the bio-electrode and the electrode having opposite polarity where said aqueous carrier includes an electrolyte and reacting an effective amount of an organelle substrate at the bioelectrode for releasing a ionic product in said aqueous carrier thereby providing a current to the electrode having opposite polarity. This embodiment of the method can also include capturing metabolic flux data during the reaction when an organelle modulating agent is present in the aqueous carrier and when an organelle modulating agent is not present and then comparing the data and determining the metabolic state of the organelle when the organelle modulating agent is present.

Another embodiment could include providing an organelle-modified bioelectrode that is electrically coupled to a second electrode of opposite polarity in a circuit and contacting said bioelectrode with an aqueous carrier that contains a biologically acceptable electrolyte and provides a portion of said circuit, an effective amount of a potential organelle modulating agent and an effective amount of an organelle substrate. This embodiment can further include the step of reacting the substrate of said carrier at the bioelectrode to form an ionic product that is released into the aqueous carrier-containing electrolyte to thereby provide a current at the second electrode when the circuit is closed. This method can use one or both of said electrodes to obtain a metabolic flux data set during said reaction and comparing those data to a control metabolic flux data set obtained under the same conditions in the absence of the potential organelle modulating agent, thereby determining the metabolic state of the organelle in the presence of the potential organelle modulating agent.

The step of obtaining the metabolic flux data from the current measurement can be performed by using an ammeter or other current measuring device to measure the current and then converting and storing representative metabolic flux data. A comparator function can be used to compare the metabolic flux data obtained and known data in order to determine the metabolic state.

The method can further include providing an mitochondria-modified bioanode and exposing the bioanode to a substrate fluid containing an inhibitor at a first concentration and oxidizing, reducing, or altering said substrate at said bioelectrode to form an oxidant, reductant, or modified substrate. The method further including releasing the oxidant, reductant, or modified substrate across an electrolyte or pro-electrolyte with having a salt bridge and further reducing, oxidizing, or altering said oxidant, oxidant, reductant, or modified substrate at an electrode.

A data set can be measured during the oxidation reducing step, and the data set can be selected from the group consisting of electrical current, open circuit potential, metabolic energy conversion, or coupled spectroscopic biochemical technique and combinations thereof. A first mitochondrial metabolic state can be determined, and the first mitochondrial metabolic state can be compared to a second mitochondrial metabolic state to determine the effect of said inhibitor on mitochondrial function.

The method can be implemented using an organelle-modified bio-electrode circuit including a mitochondria-modified anode and a cathode contacting an aqueous mitochondria substrate solution and separated by an ion selective salt bridge, where the cathode compartment of the circuit contains an electrolyte. The anode and cathode can be connected to an output adapted for measurement. A current measuring device adapted to measure a current value at the output, such as an ammeter, can be used to measure current and the current measurement can be converted and the current value can be stored in a storage device in a manner as representative of metabolic flux data. A comparator function adapted to compare the representative metabolic flux data with predetermined metabolic flux data and the metabolic flux comparison data can be stored in the storage device. A computing device can be utilized that is operable to analyze the metabolic flux comparison data to determine metabolic state.

Each of the patents, patent applications and articles cited herein is incorporated by reference. The use of the article "a" or "an" is intended to include one or more.

Because various changes could be made in the above methods without departing from the scope of the invention, it is intended that all matter contained in the above description or shown in the accompanying drawings shall be interpreted as illustrative and not in a limiting sense. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims.

What is claimed:

1. A method for monitoring the metabolic state of an organelle comprising the steps of:
   electrically coupling an organelle-modified bio-electrode to an electrode having opposite polarity by contacting an aqueous carrier between the bio-electrode and the electrode having opposite polarity where said aqueous carrier includes an electrolyte and reacting an effective amount of an organelle substrate at the bio-electrode for releasing a ionic product in said aqueous carrier thereby providing a current to the electrode having opposite polarity;
   capturing metabolic flux data during a reaction when an organelle modulating agent is present in the aqueous carrier and capturing control metabolic flux data when the organelle modulating agent is not present, comparing the metabolic flux data with the control metabolic flux data and determining a metabolic state of the organelle when the organelle modulating agent is present; and
   determining organelle metabolic activity as a function of metabolic substrate to determine modulating agent toxicity.

2. The method as recited in claim 1, where the organelle-modified bio-electrode is a mitochondria-modified bioelectrode and the step of determining the metabolic state is the step of determining mitochondrial metabolic activity as a function of metabolic substrate to determine drug toxicity.

3. The method as recited in claim 2, where the step of determining mitochondrial metabolic activity is the step of directly assaying mitochondrial activity by wiring the mitochondria to a carbon electrode surface and intercepting and rerouting electrons to a separate electrode and directly measuring current.

4. The method as recited in claim 3, where the organelle modulating agent is selected from a group consisting of an inhibitor, an activator, an uncoupler, an enhancement agent, and a combination thereof.

5. A method for monitoring the metabolic state of an organelle in the presence of a potential organelle modulating agent comprising the steps of:
   providing at least a first organelle-modified bioelectrode that is electrically coupled to a second electrode of opposite polarity in a circuit;
   contacting said first bioelectrode with an aqueous carrier that contains a biologically acceptable electrolyte and provides a portion of said circuit, an effective amount of a potential organelle modulating agent and an effective amount of an organelle substrate;
   reacting the substrate of said carrier at the bioelectrode to form an ionic product that is released into the aqueous carrier-containing electrolyte to thereby provide a current at the second electrode when the circuit is closed;
   obtaining a metabolic flux data set during said reaction using one or both of said electrodes and comparing those data to a control metabolic flux data set obtained under the same conditions in the absence of the potential organelle modulating agent, thereby determining a metabolic state of the organelle in the presence of the potential organelle modulating agent; and
   determining organelle metabolic activity as a function of metabolic substrate to determine modulating agent toxicity.

6. The method of claim 5, wherein said organelle is selected from the group consisting of a mitochondrion, a mitoplast, a chloroplast, a thylakoid, and a combination thereof.

7. The method of claim 6, wherein said organelle is a mitochondrion.

8. The method of claim 7, wherein said mitochondrion is from an animal cell, a plant cell, or a fungal cell.

9. The method of claim 5, wherein said bioelectrode comprises a material selected from the group consisting of a carbon-based material, a metallic conductor, a semiconductor, a metal oxide, a modified conductor, and combinations thereof.

10. The method of claim 9, wherein said bioelectrode comprises a carbon-based material selected from the group consisting of carbon cloth, carbon paper, carbon screen printed electrode, carbon black, carbon powder, carbon fiber, single-walled carbon nanotube, double-walled carbon nanotube, multi-walled carbon nanotube, carbon nanotube array, diamond-coated conductor, glass carbon, mesoporous carbon, graphite, uncompressed graphite worms, delaminated purified flake graphite, high performance graphite, highly ordered pyrolytic graphite, polycrystalline graphite, amorphous carbon, an allotrope of carbon or modified allotrope of carbon, an organic conductive polymer, a redox polymer, a polymer composite, and a combination thereof.

11. The method of claim 5, wherein said substrate is selected from the group consisting of a $C_2$-$C_{24}$ fatty acid, a mono-, di- or triglyceride of said $C_2$-$C_{24}$ fatty acid or a mixture thereof, an amino acid, ammonia, urea, an amine compound, lactate, pyruvate, acetyl-CoA, malate, fumarate, succinate, oxaloacetate, ketoglutarate, flavin, ATP, NADH, NADPH, hydrogen, a cytochrome, oxygen, a mono- or disaccharide, and a combination thereof.

12. The method of claim 5, wherein said biologically acceptable electrolyte is solid or liquid.

13. The method of claim 5, wherein said biologically acceptable electrolyte is selected from the group consisting of sodium or potassium chloride, sodium or potassium nitrate, a sodium or potassium phosphate salt, a sodium or potassium carbonate salt, and a combination thereof.

14. The method of claim 5, wherein said potential organelle modulating agent is selected from the group consisting of diazoxide, oligomycin, rotenone, antimycin, esomeprazole, cyanide ion, salicylic acid, valproic acid, nitric oxide, and a combination thereof.

15. The method of claim 5, wherein said potential organelle modulating agent is a pharmaceutical drug or drug candidate.

16. The method of claim 5, wherein said second electrode comprises a material selected from the group consisting of carbon, gold, platinum, rhodium, palladium, a transition metal, a transition metal oxide, a metalloid, a metal compound, a conductor, semiconductor, and a combination thereof.

* * * * *

UNITED STATES PATENT AND TRADEMARK OFFICE
CERTIFICATE OF CORRECTION

PATENT NO. : 8,845,879 B2  
APPLICATION NO. : 13/301773  
DATED : September 30, 2014  
INVENTOR(S) : Shelley Minteer, Abdul Waheed and Robert Arechederra Page 1 of 1

It is certified that error appears in the above-identified patent and that said Letters Patent is hereby corrected as shown below:

Title page, item 75, should read as follows:

INVENTOR(S): Shelley Minteer, Abdul Waheed, Robert Arechederra

Signed and Sealed this  
Seventeenth Day of November, 2015

Michelle K. Lee  
*Director of the United States Patent and Trademark Office*